(12) United States Patent
Yarunin et al.

(10) Patent No.: US 10,968,478 B2
(45) Date of Patent: Apr. 6, 2021

(54) METHODS AND REAGENTS FOR REVERSE-TRANSCRIPTION POLYMERASE CHAIN REACTION

(71) Applicant: Global Life Sciences Solutions Operations UK Ltd, Sheffield (GB)

(72) Inventors: Alexander Yarunin, Cardiff South (GB); Peter James Tatnell, Cardiff South (GB); Kathryn Louise Lamerton, Cardiff South (GB); Rebecca Ngaire Fullerton, Bulwark (GB)

(73) Assignee: Global Life Sciences Solutions Operations UK Ltd, Sheffield (GB)

(*) Notice: Subject to any disclaimer, the term of this patent is extended or adjusted under 35 U.S.C. 154(b) by 452 days.

(21) Appl. No.: 15/533,714

(22) PCT Filed: Dec. 18, 2015

(86) PCT No.: PCT/US2015/066576
§ 371 (c)(1),
(2) Date: Jun. 7, 2017

(87) PCT Pub. No.: WO2016/106111
PCT Pub. Date: Jun. 30, 2016

(65) Prior Publication Data
US 2017/0321250 A1 Nov. 9, 2017

(30) Foreign Application Priority Data
Dec. 23, 2014 (GB) .................................... 1423076

(51) Int. Cl.
| | | |
|---|---|---|
| C12Q 1/68 | (2018.01) | |
| C12Q 1/686 | (2018.01) | |
| C07H 1/00 | (2006.01) | |
| C07H 21/02 | (2006.01) | |
| C12Q 1/6806 | (2018.01) | |
| C12Q 1/6848 | (2018.01) | |

(52) U.S. Cl.
CPC ............ *C12Q 1/686* (2013.01); *C07H 1/00* (2013.01); *C07H 21/02* (2013.01); *C12Q 1/6806* (2013.01); *C12Q 1/6848* (2013.01); *C12Y 207/07007* (2013.01); *C12Y 207/07049* (2013.01)

(58) Field of Classification Search
CPC ..... C12Q 1/686; C12Q 1/6806; C12Q 1/6848
See application file for complete search history.

(56) References Cited

U.S. PATENT DOCUMENTS

| | | | |
|---|---|---|---|
| 4,962,022 A | 10/1990 | Fleming et al. | |
| 6,436,638 B1 | 8/2002 | De Leon et al. | |
| 8,314,220 B2 | 11/2012 | Mullinax et al. | |
| 9,260,711 B2 * | 2/2016 | Lamerton ............ | C12Q 1/6848 |
| 2002/0119465 A1 | 8/2002 | Zhao et al. | |
| 2002/0168658 A1 | 11/2002 | Weissman et al. | |
| 2003/0008280 A1 | 1/2003 | Goebel et al. | |
| 2003/0073830 A1* | 4/2003 | Heath ................ | C12N 15/1006 536/25.4 |
| 2003/0078380 A1 | 4/2003 | Heath et al. | |
| 2005/0158710 A1 | 7/2005 | Tsang et al. | |
| 2005/0266468 A1 | 12/2005 | Bedzyk | |
| 2007/0243601 A1 | 10/2007 | Korpimaki et al. | |
| 2008/0003575 A1 | 1/2008 | Michalik et al. | |
| 2008/0124768 A1 | 5/2008 | Mueller et al. | |
| 2009/0137008 A1 | 5/2009 | Gong et al. | |
| 2009/0203531 A1* | 8/2009 | Kurn ..................... | C12Q 1/686 506/6 |
| 2010/0136542 A1 | 6/2010 | Lee et al. | |
| 2011/0117540 A1* | 5/2011 | Cary .................... | C12N 15/101 435/5 |
| 2011/0184162 A1 | 7/2011 | Ghawana et al. | |
| 2012/0003645 A1* | 1/2012 | Yim ..................... | C12Q 1/6848 435/6.11 |
| 2013/0203122 A1 | 8/2013 | Gong et al. | |
| 2014/0004509 A1 | 1/2014 | Nelson et al. | |
| 2014/0030719 A1 | 1/2014 | Kwon et al. | |
| 2014/0113294 A1 | 4/2014 | Horton et al. | |
| 2019/0078154 A1 | 3/2019 | Yarunin et al. | |

FOREIGN PATENT DOCUMENTS

| | | |
|---|---|---|
| EP | 1050587 A2 | 11/2000 |
| JP | 2010200660 A | 9/2010 |
| WO | 2005/076908 A1 | 8/2005 |
| WO | 2008/150998 A1 | 12/2008 |
| WO | 2010/029520 A1 | 3/2010 |
| WO | 2012/062200 A1 | 5/2012 |

OTHER PUBLICATIONS

Nagai (Biochemistry and Molecular Biology International vol. 44, No. 1, Jan. 1998, pp. 157-163) (Year: 1998).*
Pastorino, et al., "Development of a TaqMan® RT-PCR assay without RNA extraction step for the detection and quantification of African Chikungunya viruses," Journal of Virological Methods 124 (2005) (pp. 65-71).
Takekawa, et al., "Rapid Diagnosis of Avian Influenza Virus in Wild Birds: Use of a Portable rRT-PCR and Freeze-dried Reagents in the Field," Journal of Visualized Experiments, Aug. 2011 (6 pgs).
PCT International Search Report and Written Opinion for PCT Application No. PCT/US2015/066584 dated Mar. 25, 2016 (9 pages).
PCT International Search Report and Written Opinion for PCT Application No. PCT/US2015/066715 dated Nov. 2, 2016 (9 pages).
GB Search Report for GB Application No. 1423080.9 dated Oct. 1, 2015 (5 pages).
GB Search Report for GB Application No. 1423082.5 dated Oct. 1, 2015 (5 pages).

(Continued)

*Primary Examiner* — Jezia Riley
(74) *Attorney, Agent, or Firm* — Eversheds Sutherland (US) LLP

(57) ABSTRACT

The present invention provides a method of amplifying an RNA molecule in a biological sample by reverse transcription PCR (RT-PCR), wherein the RT-PCR is carried out in a solution comprising a polar aprotic solvent; a serum albumin, and a polyol.

38 Claims, 14 Drawing Sheets

Specification includes a Sequence Listing.

(56) References Cited

OTHER PUBLICATIONS

Farrell et al., "Bovine Serum Albumin Further Enhances the Effects of Organic Solvents on increased Yield of Polymerase Chain Reaction of GC-rich Templates," BMC Research Notes, 2012, 5:257 (8 pages).

PCT International Search Report and Written Opinion for PCT Application No. PCT/US2015/066576 dated Mar. 18, 2016 (8 pages).

GB Search Report for GB Application No. 1423076.7 dated Sep. 18, 2015 (4 pages).

Sairkar et al., "Optimization of DNA Isolation Process and Enhancement of RAPD PCR for low quality genomic DNA of Terminalia arjuna," Journal of Genetic Engineering and Biotechnology, 2013, 11:17-24.

Simonovic et al., "Dimethyl Sulfoxide Improves Sensitivity and Specificity of RT-PCR and QRT-PCR Amplification of Low-Expressed Transgenes," Arch. Biol. Sci., 2012, 64(3):865-876.

* cited by examiner

Response Score Average

Actual by Predicted Plot

Summary of Fit

| | |
|---|---|
| RSquare | 0.912151 |
| RSquare Adj | 0.803386 |
| Root Mean Square Error | 0.659173 |
| Mean of Response | 0.6875 |
| Observations (or Sum Wgts) | 48 |

Analysis of Variance

| Source | DF | Sum of Squares | Mean Square | F Ratio |
|---|---|---|---|---|
| Model | 26 | 94.74336 | 3.64398 | 8.3864 |
| Error | 21 | 9.12470 | 0.43451 | Prob > F |
| C. Total | 47 | 103.86806 | | <.0001* |

Residual by Predicted Plot

Sorted Parameter Estimates

| Term | Estimate | Std Error | t Ratio | Prob>\|t\| |
|---|---|---|---|---|
| DMSO | 1.3586834 | 0.199008 | 6.83 | <.0001* |
| Glycerol | 0.995585 | 0.200241 | 4.97 | <.0001* |
| DTT | -0.922537 | 0.197771 | -4.66 | 0.0001* |
| (BSA-0.5)*(Glycerol-0.5)*(DTT-0.47917) | 2.8638754 | 0.818885 | 3.50 | 0.0021* |
| (BSA-0.5)*(DTT-0.47917)*(Betaine-0.52083) | -2.729562 | 0.843364 | -3.24 | 0.0040* |
| (DMSO-0.5)*(DTT-0.47917) | -1.253834 | 0.405018 | -3.10 | 0.0055* |
| (DMSO-0.5)*(Glycerol-0.5)*(DTT-0.47917) | 2.4960827 | 0.833349 | 3.00 | 0.0069* |
| (DMSO-0.5)*(Triton-0.47917) | -1.143757 | 0.416178 | -2.75 | 0.0120* |
| (Glycerol-0.5)*(Betaine-0.52083) | -1.099048 | 0.40816 | -2.69 | 0.0136* |
| (BSA-0.5)*(Triton-0.47917)*(DTT-0.47917) | -2.141869 | 0.83676 | -2.56 | 0.0183* |
| (DMSO-0.5)*(Triton-0.47917)*(DTT-0.47917) | -2.061349 | 0.853265 | -2.42 | 0.0249* |
| (Glycerol-0.5)*(Triton-0.47917)*(Betaine-0.52083) | -1.717675 | 0.831589 | -2.07 | 0.0514 |
| (Triton-0.47917)*(DTT-0.47917)*(Betaine-0.52083) | -1.630126 | 0.80773 | -2.02 | 0.0565 |
| (BSA-0.5)*(Triton-0.47917) | -0.785031 | 0.405375 | -1.94 | 0.0664 |
| (Glycerol-0.5)*(Triton-0.47917) | 0.6725359 | 0.400603 | 1.68 | 0.1080 |
| (Triton-0.47917)*(Betaine-0.52083) | 0.5563057 | 0.400559 | 1.39 | 0.1794 |
| (DMSO-0.5)*(Glycerol-0.5) | -0.525843 | 0.418339 | -1.26 | 0.2226 |
| BSA | 0.2441206 | 0.196592 | 1.24 | 0.2280 |
| Triton | -0.235942 | 0.198715 | -1.19 | 0.2484 |
| (BSA-0.5)*(Betaine-0.52083) | -0.470739 | 0.418925 | -1.12 | 0.2738 |
| Betaine | -0.183701 | 0.201448 | -0.91 | 0.3722 |
| (Triton-0.47917)*(DTT-0.47917) | -0.186815 | 0.39903 | -0.47 | 0.6445 |
| (BSA-0.5)*(DTT-0.47917) | -0.187499 | 0.406434 | -0.46 | 0.6493 |
| (Glycerol-0.5)*(DTT-0.47917) | -0.181153 | 0.40077 | -0.45 | 0.6559 |
| (DTT-0.47917)*(Betaine-0.52083) | -0.102043 | 0.404296 | -0.25 | 0.8032 |
| (BSA-0.5)*(Glycerol-0.5) | 0.0089014 | 0.410784 | 0.02 | 0.9829 |

FIG. 6B

Response Score Average

Actual by Predicted Plot

Score Average Predicted P<.0001
RSq=0.63 RMSE=1.0356

Summary of Fit

| | |
|---|---|
| RSquare | 0.628263 |
| RSquare Adj | 0.514676 |
| Root Mean Square Error | 1.035638 |
| Mean of Response | 0.6875 |
| Observations (or Sum Wgts) | 48 |

Analysis of Variance

| Source | DF | Sum of Squares | Mean Square | F Ratio |
|---|---|---|---|---|
| Model | 11 | 65.25641 | 5.93240 | 5.5311 |
| Error | 36 | 38.61164 | 1.07255 | Prob > F |
| C. Total | 47 | 103.86806 | | <.0001* |

Residual by Predicted Plot

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
ggtgaacgtg gatgaagttg                                               20

<210> SEQ ID NO 2
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2
agcacacaga ccagcacgt                                                19

<210> SEQ ID NO 3
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 3
cctcgccttt gccgatcc                                                 18

<210> SEQ ID NO 4
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 4
ggatcttcat gaggtagtca gtc                                           23

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
agaaggctgg ggctcatttg                                               20

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
aggggccatc cacagtcttc                                               20
```

METHODS AND REAGENTS FOR REVERSE-TRANSCRIPTION POLYMERASE CHAIN REACTION

CROSS REFERENCES TO RELATED APPLICATIONS

This application claims the priority benefit of PCT/US2015/066576 filed on Dec. 18, 2015 which claims priority benefit of Great Britain Patent Application No. 1423076.7 filed Dec. 23, 2014. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on May 22, 2017, is named 39176279_1.txt and is 1,505 bytes in size.

FIELD OF THE INVENTION

The present invention provides methods for reverse-transcription polymerase chain reaction. The present invention also provides compositions for use in reverse-transcription polymerase chain reactions.

BACKGROUND TO THE INVENTION

The reverse transcription polymerase chain reaction (RT-PCR) is a widely used method for amplifying RNA. In the RT-PCR reaction, a DNA molecule (termed a complementary DNA molecule, which can be abbreviated to a "cDNA molecule") is generated from a single stranded RNA template using a reverse transcriptase. The cDNA is then used as a template for exponential amplification using PCR. The cDNA sequence may be generated from the full length of the mRNA sequence or a portion of the mRNA sequence.

RT-PCR has many applications, including the diagnosis of microorganisms such as RNA-viruses, viral load monitoring during drug treatment, identification of genetic diseases, gene expression analysis and the typing of genetically modified organisms etc. Traditional RT-PCR based assays rely on RNA extraction prior to amplification, thus removing any potential RT-PCR inhibitors present in the biological material. This extraction or purification step is however, associated with several disadvantages. For example: i) it can cause the cross contamination of samples, causing the generation of false positives, which is especially critical during high throughput RNA-based screening assays such as those employed to monitor the presence of RNA-based viruses such as HIV and Ebola in blood; ii) it can be a source of infection unless the operators are following specific laboratory safety or containment measures; iii) it can be labour intensive; iv) it can be costly in terms of both material and time; and v) it does not always provide a robust and reliable method for the removal of some RT-PCR inhibitors.

One of the major challenges with developing novel methodologies for carrying out PCR directly from crude samples is the presence of compounds that inhibit the amplification of nucleic acids, such as haem in blood. One approach investigators have used to attempt to overcome this challenge is to replace the wild-type DNA polymerases with a genetically engineered enzyme that is more resistant to several common inhibitors (Al-Soud et al 1998; J. Clin. Micro 39, 485-493). Although many commercially-available products consist of mutated Taq DNA polymerases that are suitable for direct PCR, there are currently no alternatives for the direct RT-PCR amplification of RNA from crude biological samples such as blood and tissue. Inhibitor-resistant reverse transcriptase (RT) enzymes are not readily available. The development of a direct RT-PCR workflow and its incorporation into a freeze-dried format such as the GE Healthcare "Ready to Go" formulation will provide major benefits e.g. time saving and simplified workflows. Such reagents will also deliver ambient storage and transportation benefits.

SUMMARY OF THE INVENTION

According to a first aspect of the present invention, there is provided a method of amplifying an RNA molecule in a biological sample by reverse transcription PCR (RT-PCR), wherein the RT-PCR is carried out in a solution comprising a polar aprotic solvent; a serum albumin, and a polyol.

In one embodiment, the polar aprotic solvent is DMSO (dimethyl sulfoxide). In a further embodiment, the serum albumin is bovine serum albumin (BSA). In a further embodiment, the polyol is glycerol.

In a further embodiment, the solution further comprises a reducing agent. In a further embodiment, the reducing agent is dithiothreitol (DTT) or Tris(2-carboxyethyl) phosphine hydrochloride (TCEP).

In a further embodiment, the solution further comprises a non-ionic surfactant.

In a further embodiment, the solution further comprises a non-ionic surfactant and a betaine. In a further embodiment, the non-ionic surfactant is Triton X-100, Brij 56 or Brij 58. In a further embodiment, the betaine is N,N,N-trimethylglycine.

In a further embodiment, the solution comprises: DMSO at a concentration in the range 0.05 to 10% (v/v), glycerol at a concentration in the range 0.05 to 15% (v/v), and BSA at a concentration in the range 0.05 to 1.2% (w/v); or DMSO at a concentration in the range 0.05 to 10% (v/v), glycerol at a concentration in the range 0.05 to 15% (v/v), BSA at a concentration in the range 0.05 to 1.2% (w/v), and DTT or TCEP at a concentration in the range 0.5 to 20 mM; or DMSO at a concentration in the range 0.05 to 10% (v/v), glycerol at a concentration in the range 0.05 to 15% (v/v), BSA at a concentration in the range 0.05 to 1.2% (w/v), Triton X-100 at concentration in the range 0.05 to 1% (v/v); or DMSO at a concentration in the range 0.05 to 10% (v/v), glycerol at a concentration in the range 0.05 to 15% (v/v), BSA at a concentration in the range 0.05 to 1.2% (w/v), Triton X-100 at concentration in the range 0.05 to 1% (v/v), and N,N,N-trimethylglycine at a concentration in the range 0.05 to 2M.

In a further embodiment, the solution further comprises: a reverse transcriptase; a DNA polymerase; a deoxyribonucleotide triphosphate (dNTP); and at least one primer.

In a further embodiment, the biological sample has not undergone treatment with a DNase prior to the RT-PCR reaction. In a further embodiment, the biological sample has not undergone an RNA purification step prior to the RT-PCR reaction.

In a further embodiment, the method comprises subjecting the biological sample to a lysis step and a detergent neutralization step prior to contacting the biological sample with the solution or prior to the RT-PCR reaction. In a further embodiment, the lysis step is performed by contacting the biological sample with a detergent, preferably sodium dodecyl sulphate (SDS), and the detergent neutralization step is performed by contacting the sample with a cyclodextran.

In a further embodiment, the biological sample comprises a cellular sample selected from the group consisting of blood, serum, semen, cerebral spinal fluid, synovial fluid, lymphatic fluid, saliva, buccal, cervical cell, vaginal cell, urine, faeces, hair, skin, muscle, and cells grown in culture. In a further embodiment, the biological sample is derived from a virus, a eukaryotic organism or a prokaryotic organism. In a further embodiment, the biological sample is a blood sample, optionally where the blood has been treated with an anti-coagulant.

In a further embodiment, the RNA is immobilised on a solid support and the solid support is contacted with the solution. In a further embodiment, the method comprises contacting a solid support with a biological sample containing the RNA; transferring the solid support or a portion thereof to a reaction vessel (wherein the portion comprises at least some of the RNA) optionally after a washing step; and performing the RT-PCR reaction in the reaction vessel in the solution in the presence of the solid support. The washing step, if used, comprises washing the solid support with an appropriate solution.

In a further embodiment, the solid support: (a) is fibrous, optionally comprising a cellulose fibre material or a glass fibre or glass microfiber material; or (b) comprises a porous polymer, optionally a porous membrane material such as polyester, polyether sulfone (PES), polyamide (Nylon), polypropylene, polytetrafluoroethylene (PTFE), polycarbonate, cellulose nitrate, cellulose acetate or alignate; or (c) comprises aluminium oxide.

In a further embodiment, a lysis reagent is embedded on the solid support. In a further embodiment, the solid support is impregnated with one or more of (i) a weak base; (ii) a chelating agent; (iii) an anionic surfactant and (iv) a chaotropic agent such as guanidium thiocyanate.

According to a second aspect of the present invention, there is provided a dried reagent composition for amplifying an RNA molecule by reverse transcription PCR (RT-PCR), the composition comprising a sequestering reagent, a polymerase, a deoxyribonucleotide triphosphate (dNTP); a serum albumin, a polyol; and optionally a polar aprotic solvent.

In one embodiment of this second aspect, the sequestering agent is cyclodextrin. In a further embodiment, the polar aprotic solvent is DMSO (dimethyl sulfoxide), and/or the serum albumin is bovine serum albumin (BSA) and/or the polyol is glycerol.

In a further embodiment, the dried reagent comprises a reducing agent. In a further embodiment, the reducing agent is dithiothreitol (DTT) or Tris(2-carboxyethyl phosphine hydrochloride (TCEP).

In a further embodiment, the dried reagent comprises a non-ionic surfactant. In a further embodiment, the non-ionic surfactant is Triton X-100, Brij 56 or Brij 58.

In a further embodiment, the dried reagent comprises a non-ionic surfactant and a betaine, wherein the non-ionic surfactant is preferably Triton X-100, Brij 56 or Brij 58 and the betaine is N,N,N-trimethylglycine. In a further embodiment, the dried reagent comprises the polar aprotic solvent.

According to a third aspect of the present invention, there is provided a method for producing a dried reagent composition of the present invention for amplifying an RNA molecule by reverse transcription PCR (RT-PCR), comprising the steps: (a) combining a polymerase, a sequestering reagent, a dNTP, a serum albumin and a polyol, and optionally also a polar aprotic solvent, and/or a non-ionic surfactant and/or a betaine, to provide a mixture thereof; and (b) drying the mixture.

In one embodiment of this third aspect, the drying step is achieved by lyophilizing. In a further embodiment, the method comprises freezing the composition prior to the drying step.

According to a fourth aspect of the present invention, there is provided a method of amplifying an RNA molecule comprising the steps: (i) incubating the RNA molecule and the dried reagent composition of the present invention in a solution; and (ii) performing a reverse transcription PCR (RT-PCR) reaction.

In one embodiment of this method, the solution comprises DMSO that is not derived from the dried reagent composition. In a further embodiment, the dried composition does not comprise DMSO.

BRIEF DESCRIPTION OF THE DRAWINGS

FIG. 5—Model 1; BSA 1% (w/v), DMSO 5% (v/v), Triton X-100 0.5% (v/v) and betaine (1 M). Least squared model; Average score of 3.77; $R^2$=0.93. FIG. 6—Model 2; BSA 1% (w/v), DMSO 5% (v/v), glycerol 10% (v/v) and DTT (10 mM). Least squared model; Average score of 3.29; $R^2$=0.91. FIG. 7—Model 3; BSA 0.6% (w/v), DMSO 5% (v/v) and glycerol 10% (v/v). Least squared model; Average score of 3.26; $R^2$=0.63. FIG. 8—Model 4; BSA 0.6% (w/v), DMSO 5% (v/v), Glycerol 10% (v/v) and DTT 4.1 mM. Neural Net Model; Average score of 3.00; $R^2$=0.58.

DETAILED DESCRIPTION OF THE INVENTION

Figure 1:
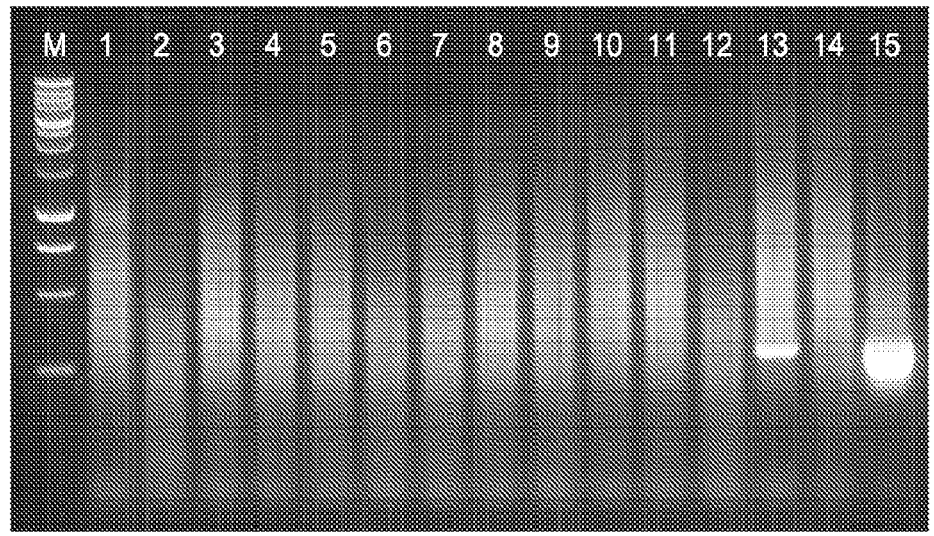
FIG. 1 is a picture of a representative agarose gel showing RT-PCR results indicating that inhibition of nucleic acid amplification was observed at blood concentration levels >0.6% (v/v). Blood concentrations ranged from 1.25% to 0.03% (v/v) and total blood RNA was added to the test samples. The degree of inhibition was assessed by the generation of the appropriately sized β-globin RT-PCR product (291 bp). 1—genomic DNA; 2—1.25% (v/v) blood; 3—1.25% (v/v) blood supplemented with blood RNA (200 ng); 4—0.6% (v/v) blood; 5—0.6% (v/v) blood supplemented with blood RNA (200 ng); 6—0.3% (v/v) blood; 7—0.3% (v/v) blood supplemented with blood total RNA (200 ng); 8—0.125% (v/v) blood; 9—0.125% (v/v) blood supplemented with blood RNA (200 ng); 10—0.06% (v/v) blood; 11—0.06% (v/v) blood supplemented with blood RNA (200 ng); 12—0.03% (v/v) blood; 13—0.03% (v/v) blood supplemented with blood RNA (200 ng); 14—Negative control and 15—Positive control (total blood RNA, 200 ng)

The present application is directed to methods and reagents for use amplifying RNA by reverse-transcription-PCR (RT-PCR). Traditional RT-PCR based assays rely on RNA extraction prior to amplification, thus removing any potential RT-PCR inhibitors present in the biological material. As highlighted above, this extraction or purification step is associated with several disadvantages. Accordingly, the present inventors carried out extensive studies to identify particular combinations of reagents and/or method steps that would allow effective RT-PCR reactions to be carried out on crude RNA samples, without the need to carry out prior-steps aimed at extracting and/or purifying RNA from the sample. The present inventors set about this goal by researching many different combinations of reagents for use in the RT-PCR reaction. The present inventors further identified optimisation steps up-stream of the RT-PCR reaction that can be employed to further enhance the process.

Accordingly, in a first aspect, the present invention relates to a method of amplifying an RNA molecule in a biological sample by reverse transcription PCR (RT-PCR), wherein the RT-PCR is carried out in a solution comprising a polar aprotic solvent; a serum albumin, and a polyol.

RT-PCR is an RNA amplification technique that is well known in the art. In RT-PCR, the RNA template is first converted into a complementary DNA (cDNA) using a reverse transcriptase. The cDNA is then used as a template for amplification using PCR. The use of RT-PCR for the detection of RNA transcript has revolutionized the study of gene expression. In RT-PCR, the cDNA is generated through the action of a reverse transcriptase. Enzymes for use in this step are well known in the art. The cDNA sequence may be generated from the full length of the mRNA sequence or a portion of the mRNA sequence. Accordingly, first-strand cDNA synthesis reactions can use oligo-dTs (short sequences of deoxy-thymine nucleotides as a complementary primer which binds to the poly-A tail providing a free 3'-OH end that can be extended by reverse transcriptase to create the complementary DNA strand). Alternatively, random primers or sequence specific primers may be employed in this step. A skilled person can readily determine the appropriate annealing and extension temperatures from the primer sequence, mRNA template and choice of reverse transcriptase using procedures well known in the art.

The amplification step comprises performing a polymerase chain reaction (PCR) on the generated cDNA sequence. It should be noted that references throughout this disclosure to amplifying a cDNA sequence encompasses amplification of either the complete cDNA sequence generated in the reverse-transcription step or a part of the cDNA sequence generated in the reverse transcription step. (PCR) is widely known in the art. For example, U.S. Pat. Nos. 4,683,195, 4,683,202, and 4,800,159; K. Mullis, Cold Spring Harbor Symp. Quant. Biol., 51:263-273 (1986); and C. R. Newton & A. Graham, Introduction to Biotechniques: PCR, 2.sup.nd Ed., Springer-Verlag (New York: 1997), the disclosures of which are incorporated herein by reference, describe processes to amplify a nucleic acid sample target using PCR amplification extension primers which hybridize with the sample target. Using PCR, the cDNA is amplified exponentially using a polymerase e.g. a DNA polymerase. PCR requires forward and reverse extension primers which hybridize with the sample target. As the PCR amplification primers are extended, using a DNA polymerase (preferably thermostable), more sample target is made so that more primers can be used to repeat the process, thus amplifying the sample target sequence. Typically, the reaction conditions are cycled between those conducive to hybridization and nucleic acid polymerization, and those that result in the denaturation of duplex molecules. To briefly summarize, in the first step of the reaction, the nucleic acid molecules of a sample are transiently heated, in order to denature double stranded molecules. Forward and reverse primers are typically present in the amplification reaction mixture at an excess concentration relative to the sample target. When the sample is cooled to a temperature conducive to hybridization and polymerization, the primers hybridize to the complementary sequence of the nucleic acid molecule at a position 3' to the sequence of the region desired to be amplified that is the complement of the sequence whose amplification is desired. Upon hybridization, the 3' ends of the primers are extended by the polymerase. The extension of the primer results in the synthesis of a DNA molecule having the exact sequence of the complement of the desired nucleic acid sample target. The PCR reaction is capable of exponentially amplifying the desired nucleic acid sequences, with a near doubling of the number of molecules having the desired sequence in each cycle. Thus, by permitting cycles of denaturation, hybridization, and polymerization, an exponential increase in the concentration of the desired nucleic acid molecule can be achieved. A preferred physical means for strand separation involves heating the nucleic acid until it is completely (>99%) denatured. Typical heat denaturation involves temperatures ranging from about 80° C. to about 105° C., for times ranging from a few seconds to minutes.

In the present invention, the template for amplification is the cDNA strand produced during the reverse transcription step. Accordingly, the PCR reaction would typically require a forward primer that anneals to the cDNA strand produced during the reverse transcription step and which is then extended using an enzyme with DNA polymerase activity to produce the complement cDNA strand. The resulting cDNA strand can then be denatured and the forward primer and a reverse primer annealed to the respective cDNA strands to allow further extension. The primers are then extended by the polymerase to replicate the cDNA sequences, and the process is then repeated multiple times.

The cocktail of reagents used for the RT-PCR reaction may comprise a reverse transcriptase enzyme for the reverse transcription step and a DNA polymerase enzyme for the PCR reaction. However, a single enzyme may also be used that is able to perform the enzymatic steps in both the reverse transcription reaction and the PCR reaction. An example of such an enzyme that is configured for DNA polymerization and reverse transcription that can be used in the present invention is rTth. Other reagents include one or more primers (described above), dNTPs (deoxynucleotide triphosphates). Suitable buffers may also be employed.

The term "primer" refers to a molecule that physically hybridizes with a target nucleic acid. The primer is capable of being extended in an amplification reaction such as a PCR reaction or in a reverse-transcription reaction. Typically, a primer can be made from, or comprise of, any combination of nucleotides or nucleotide derivatives or analogs available in the art. More typically, a primer will be in the form of an oligonucleotide. Primers may also contain one or more nucleotide alternatives or modified bases to add increased specificity and/or disrupt the efficiency of primer extension in the presence of a mis-match. Alternative bases used to enhance specificity may include Locked Nucleic Acid (LNA) bases, Peptide Nucleic Acid (PNA) bases and Inosine. The primer may be unlabelled or labelled with a detection marker.

The term "polar aprotic solvent" is used to denote a solvent that will dissolve many salts, has a comparatively high relative permittivity (or dielectric constant), e.g., greater than ca. 15, and a sizable permanent dipole moment, that cannot donate suitably labile hydrogen atoms to form strong hydrogen bonds. In a preferred embodiment, the polar aprotic solvent dissolves both polar and non-polar compounds. In a particularly preferred embodiment, the polar aprotic solvent used in the present invention is dimethyl sulfoxide (DMSO).

The polar aprotic solvent may be employed in the solution at a concentration in the range 0.05-10% (v/v). For example, the polar aprotic solvent may be used at a concentration in the range 1-9% (v/v), 2-8% (v/v), 3-7% (v/v) or 4.5-5.5% (v/v). Typically, the polar aprotic solvent may be used at a concentration of approximately 5% (v/v).

Serum albumin, often referred to simply as blood albumin, is a globular protein that in humans is encoded by the ALBgene. Serum albumin is produced by the liver, occurs dissolved in blood plasma and is the most abundant blood protein in mammals. The serum albumin that may be used in the present invention may be, for example, bovine serum albumin, human serum albumin, goat serum albumin, mammalian albumin, or any combination thereof. In a particularly preferred embodiment, the serum albumin is bovine serum albumin (BSA).

The serum albumin may be employed in the solution at a concentration in the range 0.05-1.2% (w/v). For example, the serum albumin may be used at a concentration in the range 0.1-1.2% (w/v), 0.2-1.2% (w/v), 0.3-1.2% (w/v), 0.4-1.2% (w/v), 0.5-1.2% (w/v) or 0.6-1.2% (w/v). In a preferred embodiment, the serum albumin is used at a concentration in the range of 0.5-1.1% (w/v).

The term "polyol" refers to an alcohol containing multiple hydroxyl groups. In a preferred embodiment, the polyol contains only carbon, hydrogen and oxygen atoms. In a particularly preferred embodiment, the polyol is glycerol.

The polyol may be employed in the solution at a concentration in the range 0.05-15% (v/v). For example, the polyol may be used at a concentration in the range 1-15% (v/v), 2-15% (v/v), 3-15% (v/v), 4-15% (v/v), 5-15% (v/v), 6-15% (v/v), 7-15% (v/v), 8-15% (v/v), 9-15% (v/v), 5-14% (v/v), 5-13% (v/v), 5-12% (v/v), or 5-11% (v/v). In a preferred embodiment, the polyol is used at a concentration of approximately 10% (v/v).

The solution used in the method of the present invention may further comprise one or more of a reducing agent, a non-ionic surfactant and a betaine.

In one embodiment the solution may comprise a polar aprotic solvent; a serum albumin, a polyol and a reducing agent. In one embodiment, the solution may comprise a polar aprotic solvent; a serum albumin, a polyol and a non-ionic surfactant. In one embodiment the solution may comprise a polar aprotic solvent; a serum albumin, a polyol, a non-ionic surfactant and a betaine. In one embodiment, the solution comprises a polar aprotic solvent; a serum albumin, and a polyol but does not further comprise one or more of a reducing agent, a non-ionic surfactant and a betaine.

In a preferred embodiment, the reducing agent is dithiothreitol (DTT), Tris(2-carboxyethyl phosphine (TCEP) or a combination thereof. TCEP may be employed in a salt form, preferably the hydrochloric salt.

The reducing agent may be employed in the solution at a concentration in the range 0.5-20 mM. For example, the reducing agent may be used at a concentration in the range 2-15 mM, 3-12 mM, or 3.5-10.5 mM.

The non-ionic surfactant may be employed to prevent the polymerase(s) sticking to themselves or the walls of the reaction tube (preventing loss of reagents through adsorption to tube walls). It may also aid in solubilizing the reaction containing the BSA, destabilizing secondary structures and stabilizing the polymerase (e.g. Taq polymerase). Non-ionic surfactants or detergents also have the added benefit of overcoming inhibitory effects of trace amounts of strong ionic detergents.

The non-ionic surfactant may be a non-ionic surfactant comprising a hydrophilic polyethylene oxide chain. The non-ionic surfactant may comprise both a hydrophilic polyethylene oxide chain and an aromatic hydrocarbon lipophilic or hydrophobic group such as 4-(1,1,3,3-tetramethylbutyl)-phenyl group. In a preferred embodiment, the non-ionic surfactant is 4-(1,1,3,3-Tetramethylbutyl)phenyl-polyethylene glycol.

The non-ionic surfactant may also be a polyethylene glycol hexadecyl ether of formula $C_{16}H_{33}(OCH_2CH_2)nOH$ where n is between 5 and 25, preferably between 9 and 20, and preferably still 10 or 20.

In a particularly preferred embodiment, the non-ionic surfactant is Triton X-100, Brij 56 or Brij 58, or a combination thereof. In a most preferred embodiment, the non-ionic surfactant is Triton X-100.

The non-ionic surfactant may be employed in the solution at a concentration in the range 0.05-1% (v/v). For example, the non-ionic surfactant may be used at a concentration in the range 0.1-1% (v/v), 0.2-1% (v/v), 0.3-1% (v/v), 0.4-1% (v/v), 0.1-0.9% (v/v), 0.1-0.8% (v/v), 0.1-0.7% (v/v), 0.1-0.6% (v/v), 0.3-0.7% (v/v), or 0.4-0.6% (v/v). In a preferred embodiment, the non-ionic surfactant is used at a concentration of approximately 0.5% (v/v).

Betaines are a neutral chemical compounds with a positively charged cationic functional group such as a quaternary ammonium or phosphonium cation and which typically bear no hydrogen atom directly attached to the charged atom of the cation and with a further negatively charged functional group such as a carboxylate group. In the present invention, the betaine preferably reduces the formation of secondary structure in GC-rich regions by reducing the amount of energy required to separate nucleic acid strands, and/or reducing the base pair composition dependence of DNA melting. In a particularly preferred embodiment of the present invention, the betaine is N,N,N-trimethylglycine (also known as 2-trimethylammonioacetate).

The betaine may be employed in the solution at a concentration in the range 0.05-2M. For example, the betaine may be used at a concentration in the range 0.1-2M, 0.2-2M, 0.3-2M, 0.4-2M, 0.5-2M, 0.6-2M, 0.7-2M, 0.8-2M, 0.9-2M, 0.5-1.5M, 0.6-1.4M, 0.7-1.3M, or 0.8-1.2M. In a preferred embodiment, the betaine is used at a concentration of approximately 1 M.

Examples of preferred solutions for use in the present invention comprise: a) DMSO at a concentration in the range 0.05 to 10% (v/v), glycerol at a concentration in the range 0.05 to 15% (v/v), and BSA at a concentration in the range 0.05 to 1.2% (w/v); b) DMSO at a concentration in the range 0.05 to 10% (v/v), glycerol at a concentration in the range 0.05 to 15% (v/v), BSA at a concentration in the range 0.05 to 1.2% (w/v), and DTT or TCEP at a concentration in the range 0.5 to 20 mM; (c) DMSO at a concentration in the range 0.05 to 10% (v/v), glycerol at a concentration in the range 0.05 to 15% (v/v), BSA at a concentration in the range 0.05 to 1.2% (w/v), Triton X-100 at concentration in the range 0.05 to 1% (v/v); and DMSO at a concentration in the range 0.05 to 10% (v/v), glycerol at a concentration in the range 0.05 to 15% (v/v), BSA at a concentration in the range 0.05 to 1.2% (w/v), Triton X-100 at concentration in the range 0.05 to 1% (v/v), and N,N,N-trimethylglycine at a concentration in the range 0.05 to 2M.

It will be appreciated that the solution will comprise other reagents necessary for performing a RT-PCR reaction, as discussed above. For example, the solution may further comprise a reverse transcriptase, a DNA polymerase, deoxyribonucleotide triphosphates (dNTPs); and at least one primer. As discussed above, the reverse transcriptase and the DNA polymerase may be the same enzyme (where the enzyme has the ability to carry out both reverse transcription and DNA amplification) or separate enzymes. A skilled person would recognise that further buffer reagents may also be employed, as is well known in the art.

The method of RT-PCR disclosed may be carried out on crude biological samples and/or biological samples that have not undergone RNA extraction or purification prior to the RT-PCR reaction. In one embodiment, the biological sample has not undergone treatment with a DNase prior and/or has not undergone an RNA purification step prior to the RT-PCR reaction. An example of such a purification or extraction method is acid guanidinium thiocyanate-pheno-chloroform extraction. Other examples include column-based systems such as silica-based purification.

Accordingly, the method of RNA amplification of the present invention may be carried out with significantly less "pre-processing" of the sample compared to known methods. Furthermore, the RT-PCR can take place in a "one-step" approach, where the cDNA synthesis and the PCR amplification occurs in a single tube, and both the cDNA synthesis and the PCR amplification take place in the presence of a polar aprotic solvent, a serum albumin, a polyol, and optionally, as described above, one or more of a reducing agent, a non-ionic surfactant and a betaine. However, it will be appreciated that whilst the RT-PCR reaction takes place in a solution comprising these components, further substances/solutions may be added to the solution during the reaction (e.g. between initiating the reverse transcription reaction and the performing the PCR reaction) and the invention scope will be understood to cover such additional steps. In one embodiment, no further substances/solutions are added to the solution during the reaction.

Prior to all or part of the RT-PCR reaction, the biological sample may be subjected to a lysis step. Preferably, prior to all or part of the RT-PCR reaction, the biological sample is subjected to a lysis step and a detergent neutralization. The detergent neutralisation step neutralises the detergent used in the lysis step. The lysis step is performed by contacting the biological sample with a detergent, preferably sodium dodecyl sulphate (SDS), and the detergent neutralization step is preferably performed by contacting the sample with a detergent sequesterant, preferably a cyclodextran. The cyclodextran may, for example, be selected from the group consisting of one or more of α-cyclodextrin, β-cyclodextrin, γ-cyclodextrin, 6-O-α-D-Maltosyl-β cyclodextrin, hydroxyethyl-β-cyclodextrin, hydroxypropyl-β-cyclodextrin and 2-hydroxypropyl-β-cyclodextrin or derivatives thereof. In one embodiment, the cylodextrin is selected from the group consisting of α-cyclodextrin, β-cyclodextrin, γ-cyclodextrin. In one embodiment, the cyclodextrin is α-cyclodextrin.

The biological sample may comprise a cellular sample selected from the group consisting of blood, serum, semen, cerebral spinal fluid, synovial fluid, lymphatic fluid, saliva, buccal, cervical cell, vaginal cell, urine, faeces, hair, skin, muscle, and cells grown in culture. The biological sample may be derived from a virus, a eukaryotic organism or a prokaryotic organism.

In a preferred embodiment, the biological sample is a blood sample. The blood sample may be a blood sample that has been treated with an anti-coagulant. Anticoagulants suitable for use in the present invention include heparin and substances that make $Ca^{2+}$ unavailable for clotting (e.g., EDTA, citrate, oxalate, fluoride). Preferred examples include sodium heparin, a potassium oxalate and sodium fluoride combination, EDTA and sodium citrate.

The RNA in the biological sample may be immobilised on a solid support such that the solid support, or a portion of the solid support comprising at least some of the RNA, is contacted with the solution in order to perform the RT-PCR reaction.

Solid supports for storing, transporting and archiving of nucleic acids such as filter paper or chemically modified matrices are well-known in the art. Furthermore, solid supports are commercially available that can be used directly in nucleic acid amplification reactions. Examples of solid supports are described in, for example, US 2014/0212880 A1, US 2014/0154667 A1, EP1563091 A1, WO1990003959, U.S. Pat. No. 5,496,562, the entire contents of which are incorporated herein.

The solid support may be fibrous, optionally comprising a cellulose fibre material or a glass fibre or glass microfiber material. The solid support may comprise a porous polymer, optionally a porous membrane material such as polyester, polyether sulfone (PES), poly amide (Nylon), polypropylene, polytetrafluoroethylene (PTFE), polycarbonate, cellulose nitrate, cellulose acetate or alignate. In a preferred embodiment, the solid support is a cellulose-based matrix. The solid support may comprise a lysis reagent and a sequestering reagent. The solid support may be impregnated with a weak base; a chelating agent; an anionic surfactant and a chaotropic agent such as guanidium thiocyanate. Examples of suitable commercially available matrices are in the form of FTA™ and FTA™ Elute card (GE Healthcare). The matrix may be in the form of a pre-punched disc. Where a solid support is employed, the RT-PCR reaction may take place at the surface of the solid support whilst the solid support is present in the solution.

The method of the invention can be used, for example, either in a single reaction well or a high-throughput 96-well format in combination with automated sample processing as described by Baron et al., (2011, Forensics Science International: Genetics Supplement Series, 93, e560-e561). This approach would involve a minimal number of steps and increase sample throughput. The risk of operator-induced error, such as cross-contamination is also reduced since this procedure requires fewer manipulations compared to protocols associated with currently used, more labour intensive kits (e.g. QIAmp DNA blood mini kit, Qiagen). The risk of sample mix-up is also reduced since the procedure requires few manipulations. Importantly, the method is readily transferable to a multi-well format for high-throughput screening. The present invention can thus improve sample processing for carrying out PCR reactions to aid genetic interrogations. The invention can be conducted in a 96 well/high throughput format to facilitate sample handling and thus eliminate batch processing of samples.

The findings of the present invention can be utilised to generate improved dried reagent compositions for use in amplifying an RNA molecule by RT-PCR. Dried reagent compositions for use in RT-PCR are commercially available, for example, the illustra Ready-To-Go RT-PCR beads (GE Healthcare). These Ready-To-Go RT-PCR Beads are stable at room temperature and designed for performing single-tube one-step reverse transcription-PCR. Each room-temperature-stable bead contains M-MuLV Reverse Transcriptase, RNase Inhibitor, buffer, nucleotides, and Taq DNA Polymerase. The only additional reagents that need be added to the beads to perform the RT-PCR are water, template RNA, and primers.

The Ready-To-Go Bead format significantly reduces the number of pipetting steps, thereby increasing reproducibility of the RT-PCR technique and minimizing risk of contamination and RNA degradation. Ready-To-Go RT-PCR Beads are provided in either thin walled 0.5 ml or 0.2 ml tubes compatible with most thermocyclers. The 0.2 ml tubes come assembled in a 96-well (8×12) plate format that allows individual strips of eight tubes to be easily removed. This flexibility allows use of either the entire 96-well plate, strips of eight or individual 0.2 ml tubes. Each package of Ready-To-Go RT-PCR Beads contains: RT-PCR beads, control reactions and pd(N)6 and oligo(dT) cDNA primers.

Further examples of the use of dried compositions (e.g. in the form of beads or cakes) for use in PCR reactions, and methods of making such compositions, are described in WO2014064169 A1, U.S. Pat. No. 5,593,824, EP2063866 B1 and U.S. Pat. No. 5,565,318, the entire contents of which are incorporated herein.

Accordingly, in a second aspect, the invention provides a dried reagent composition for amplifying an RNA molecule by reverse transcription PCR (RT-PCR), the composition comprising a sequestering reagent, a DNA polymerase, a reverse transcriptase, deoxyribonucleotide triphosphates (dNTPs); a serum albumin, a polyol; and optionally a polar aprotic solvent.

The serum albumin, polyol and polar aprotic solvent may be chosen from any of the embodiments described above with respect to the first aspect of the invention. In a preferred embodiment the polar aprotic solvent, if present, is DMSO, the serum albumin is BSA and the polyol is glycerol.

The dried reagent composition may further comprise one, two or all of an agent selected from the group consisting of: a reducing agent, preferably DTT or TCEP; a non-ionic surfactant, preferably Triton X-100, Brij 56 or Brij 58; and a betaine, preferably N,N,N-trimethylglycine.

The dried reagent composition may comprise, for example: a) DMSO; glycerol; and BSA b) DMSO; glycerol; BSA; and DTT or TCEP (c) DMSO; glycerol; BSA; Triton X-100; and (d) DMSO; glycerol; BSA; Triton X-100; and N,N,N-trimethylglycine.

The enzyme performing the reverse transcriptase activity and the polymerase activity may be the same or different enzymes. As mentioned above, a single enzyme may also be used that is able to perform the enzymatic steps in both the reverse transcription reaction and the PCR reaction. In a preferred embodiment, the reverse transcriptase and the DNA polymerase are different enzymes.

In one embodiment, the polymerase is an OmniKlen Taq (OKT) Polymerase. Alternatively, the polymerase may be selected from the group consisting of T4 DNA Polymerase, Pol I and Klenow Fragment, T4 DNA Polymerase, Modified Bacteriophage T7 DNA Polymerase, Terminal Deoxynucleotide Transferase, Bst Polymerase, Taq Polymerase, Tth polymerase, Pow Polymerase, Vent Polymerase, Pab Pol I DNA Polymerase, Thermus thermophiles, Carboxydothermus hydrogenoformans, SP6 and SP7 RNA polymerase. In a further embodiment, the reverse transcriptase is M-MuLV Reverse Transcriptase, and the polymerase is Taq DNA Polymerase.

In one embodiment, the sequestering agent is a cyclodextrin. The cyclodextrin may be selected from a group consisting of α-cyclodextrin, β-cyclodextrin, γ-cyclodextrin and derivatives thereof. Cyclodextrin could consist of a group consisting of 6-O-α-D-Maltosyl-β cyclodextrin, hydroxyethyl-β-cyclodextrin, hydroxypropyl-β-cyclodextrin and 2-hydroxypropyl-β-cyclodextrin. The sequestrant is preferably α-cyclodextrin. The sequestering reagent is preferably not a chelating agent. A chelating agent is a chemical compound that combines with a metal to form a chelate, often used to trap heavy metal ions (Collins English Dictionary, © HarperCollins Publishers 2003).

In a further embodiment, the dried reagent composition comprises a least one primer.

In a further embodiment, the dried reagent composition additionally comprises an excipient mix. The term "excipient mix" is used herein to denote additives or ingredients used to make up a preparation or mixture and for example may comprise of PCR buffer, Ficoll 70, Ficoll 400, Melezitose, Trehalose, and stabilising proteins.

The term "PCR buffer" is used herein to denote a buffer necessary to create optimal conditions for activity of a DNA polymerase and/or a reverse transcriptase, and for example may comprise of Tris-HCl, KCl, $MgCl_2$, and gelatin.

In a further embodiment, the dried reagent composition additionally comprises an exchange buffer or buffer composition. The term "exchange buffer" is used herein to denote a buffer used for the removal of small ionic solutes, whereby one buffer is removed and replaced with another alternative buffer and for example may comprise of Tris/HCl, $CaCl_2$, a detergent, RE960, $MgCl_2$, and KCl.

The RT-PCR dried reagent composition may typically contain buffer, dATP, dCTP, dGTP, dTTP, Taq DNA Polymerase, M-MuLV reverse transcriptase, and an RNase inhibitor. The composition may further comprise one or more stabilizers. The dried composition, e.g. a bead or cake, may be formulated such that, when it is reconstituted (e.g to a volume of 50 µl), the concentration of each dNTP is approximately 200 µM in approximately 10 mM Tris-HCl (approximately pH 9.0), approximately 60 mM KCl, and approximately 1.5 mM $MgCl_2$.

The concentration of polar aprotic solvent, albumin, polyol, reducing agent, non-ionic surfactant and betaine (to the extent they are present in the dried composition) may be such that, when the dried composition is incubated in a volume of solution for the RT-PCR reaction (e.g. in the range 10 to 200 µl, such as 20 to 100 µl, and preferably approximately 50 µl), these components achieve the concentration levels set out above with respect to the first aspect of the invention.

In a further embodiment, the dried reagent composition is a lyophilized composition. The advantage of dried or lyophilised formulations of the RT-PCR reagents is that they can be easily solubilised by the addition of water, thus saving operator time and facilitating operator usage. To minimise operator error, the dried reagent mixture can be pre-dispensed into the reaction vessel, such as the well of a multi-well plate. The preformulated, predispensed, ambient-temperature-stable beads or cakes allow amplification reactions to be carried out within a single well or reaction vessel and ensure greater reproducibility between reactions, minimize pipetting steps, and reduce the potential for pipetting errors and contamination.

The dried reagent composition can be used, for example, either in a single reaction well or a high-throughput 96-well format in combination with automated sample processing as described above.

In one embodiment, the dried reagent composition comprises DMSO. In another embodiment, the dried reagent composition does not comprise DMSO and the DMSO is added as part of the RT-PCR reaction mixture that is added to the dried composition for carrying out the RT-PCR reaction.

In a third aspect, the present invention provides a method for producing a dried reagent composition as defined in the second aspect for amplifying an RNA molecule by reverse transcription PCR (RT-PCR), comprising the steps: combining a polymerase; a sequestering reagent; a dNTP; a serum albumin; and a polyol; and optionally also a polar aprotic solvent, and/or a non-ionic surfactant and/or a betaine, to provide a mixture thereof; and drying the mixture.

The drying step is preferably achieved by lyophilizing the mixture. The mixture may be subjected to a freezing step prior to the drying step.

It will be appreciated that other ingredients may be included in the mixture of the third aspect, for example one or more of the further ingredients that may be present in the dried composition of the second aspect of the invention, and the inclusion of such further ingredients in the mixture described in the third aspect of the invention shall be considered to be within the scope of the method of the third aspect.

In a fourth aspect, the present invention provides a method of amplifying an RNA molecule comprising the steps: (i) incubating the RNA molecule and the dried reagent composition of the second aspect of the present invention; and (ii) performing a reverse transcription PCR (RT-PCR) reaction.

In step (i) of the fourth aspect, water is added to the RNA molecule. Step (i) may also comprise adding primers for the reverse transcription reaction and/or PCR reaction. Step (i) may also comprise adding the non-polar aprotic solvent, such as DMSO, for example where the dried reagent does not comprise DMSO. The RNA molecule may be part of a biological sample described above. The RNA molecule may be immobilised on a solid support as described above. The RNA molecule may be part of a biological sample that has not undergone treatment with a DNase prior to the RT-PCR reaction and/or has not undergone an RNA purification step prior to the RT-PCR reaction.

The present invention will now be described with reference to the following non-limiting examples.

Experimental Outline

The aim of this study was to identify a reverse transcriptase-polymerase chain reaction (RT-PCR) formulation which would directly amplify a RT-PCR product from the RNA present in crude biological samples. Experimentation focussed on the amplification of RNA directly from diluted whole blood, cultured cells and biological samples applied to chemically-coated FTA sample collection cards (GE Healthcare) using liquid and freeze-dried reagents such as the illustra Ready-to-Go (RTG) RT-PCR reagent (GE Healthcare). Whole blood is considered to be a difficult source from which to amplify nucleic acids due to the presence of multiple inhibitors. The illustra RTG beads provide temperature stable reagents designed for performing single-tube one-step RT-PCR. Each room temperature-stable bead contains M-MuLV Reverse Transcriptase, RNase inhibitor, buffer, nucleotides, and wildtype Taq DNA Polymerase. The only additional reagents required are water, RNA, and the appropriate primers and these are supplied by the user depending upon their specific application.

Initially, experimental work focussed on the development of an RT-PCR protocol in liquid formulations using AffinityScript RT, and the mutated taq DNA polymerase Omniklentaq in combination with the PCR enhancer cocktail PEC-1. Omniklentaq is an engineered enzyme that is considered to be inhibitor resistant. This initial work attempted the amplification of RNA directly from whole EDTA-treated blood samples and investigated a range of blood concentrations. Results (not shown) demonstrated that Omniklentaq in combination with PEC-1 alone was not able to overcome RT-PCR inhibition when using blood as the RNA source even at extremely low blood concentrations [final blood diluted as low as 0.03% v/v with phosphate buffered saline (PBS)].

Later experiments focussed on developing i) an efficient detergent-based cellular lysis method suitable for direct RT-PCR and ii) a model system that enabled the amplification of RNA from diluted blood from which a more efficient system could be developed.

Results from initial experimentation showed that RNA could be successfully amplified from up to 0.1% v/v blood using a combination of RTG RT-PCR beads with the addition of BSA 0.6 (w/v). Therefore the combination of diluted blood and the RT-PCR RTG beads demonstrated that RT-PCR products could be generated albeit at a relatively low yield.

In order to increase direct RT-PCR product yield, the effect on nucleic acid amplification of a number of chemicals was investigated. A formal statistically-relevant Design of Experiment (DOE) was performed and the results highlighted several combinations of chemicals that generated significantly higher yields of RT-PCR product compared a control system. Therefore, RT-PCR product yield could be increased by adding specific combinations of chemical to the RT-PCR RTG bead formulation. Later these combinations were also shown to deliver increased RT-PCR product yield when used in different formats including a liquid RT-PCR formulation and the direct amplification of RNA molecules from blood, tissue and biological material applied to solid supports such as GE Healthcare/Whatman FTA sample collection cards.

Materials

| Material | Supplier | Code | Lot No. |
|---|---|---|---|
| $MgCl_2$ | Invitrogen | YO2016 | 564749 |
| α Cyclodextrin | Fluka | 28705-5G | BCBC9148V |
| AffinityScript RT | Agilent Technologies | 600107 | 000621324 |
| human blood total RNA | Clontech | 636592 | 1002007 |
| 10% BSA | Calbiochem | 126615 | D00100942 |
| RNase Free $H_2O$ | Fresenius KABI | 22-96-985 | 12W204 |
| OmniklenTaq | DNA Polymerase Technology | 350 | 032210350 (RT) 082210RB10 (buffer) |
| Taq DNA polymerase (cloned) | GE Healthcare | 27-0798-04 | |
| PEC 1 Buffer | DNA polymerase Technology | E600 | 3147715566 |
| Whole Human Blood | Tissue Solutions | N/A | SAG029019 |
| Human genomic DNA | Applied Biosystems | 360486 | 0902066 |
| β-Globin Primer Forward | Sigma | N/A | HA02431160-002 |
| β-Globin Primer Reverse | Sigma | N/A | HA02431163-002 |
| β-Actin Primer Forward | Sigma | N/A | HA03324903 |
| β-Actin Primer Reverse | Sigma | N/A | HA03324904 |
| GAPDH Forward primer | Sigma | N/A | HA03867051 |
| GAPDH Reverse primer | Sigma | N/A | HA03867052 |
| 100 mM dNTP's | Bioline | BIO-39025 | DM-S11G |
| TAE buffer | BioRad | 161-0743 | 11193412012 |
| Gel Red | Biotuim | 41003-0.5 | 12G1008 |
| Agarose | USB | 75817 100 g | 4121019 |
| 1Kb Marker | Promega | G571A | 30236902 |
| 6x Loading Dye | Promega | G190A | 30738805 |
| Random hexamers | GEHC | 32370 | 4663305 |
| SDS | Sigma | 71736-100ML | BCBH9299V |
| Oligo d(T) | GEHC | 32368 | 5479499 |
| AffinityScript RT buffer | Agilent technologies | 600100-52 | 0006112143 |
| DMSO | Sigma | D2650 | RNBC3643 |
| Glycerol | Fischer Scientific | BP229-1 EC200-289-S | 116971 |
| Betaine (5M) | Sigma | BO300-1VL | SLBC7265 |
| 100 mM DTT | Promega | P1171 | 0006108106 |
| Triton X-100 | Sigma | T8787-50ML | MKBL3099V |
| RT-PCR RTG beads | GEHC | 279260D-96 | 7561620 |
| RNase-free microcentrifuge tubes | Ambion | AM12450 | 1207097 |

Direct RT-PCR Method

A RT-PCR process was initially performed using AffinityScript RT (Agilent Technologies), Omniklentaq DNA polymerase and PCR enhancer cocktail 1 (DNA Polymerase Technology). The reaction mixture consisted of EDTA anticoagulated human blood diluted to 1.25% to 0.03% (v/v), with PBS either in the presence (200 ng) or absence of total RNA, and either Oligo (d)T or random hexamers. Purified total RNA was derived from either human blood (Clontech) or total RNA extracted from human HeLa cells using the illustra RNAspin kit (GE Healthcare) following the manufacturer's instructions. Before use the RNA was incubated at 65° C. for 5 min then allowed to cool at room temperature for 10 minutes.

Following the incubation, an AffinityScript RT reaction was established according to the manufacturer's recommendation. This consisted of ×10 buffer, DDT, 100 mM dNTPS and AffinityScript RT enzyme (2 units). The RT reaction was performed at 42° C. for 60 min followed by an enzyme heat inactivation step of 70° C. for 15 min.

For the PCR reaction, thermocycling conditions were; 94° C., 4 min, followed by 32 cycles of 94° C., 1 min, 55° C., 1 min and 68° C. 2.5 min. To differentiate amplified PCR products derived from RNA and genomic DNA, primers were designed at exon boundaries to amplify a 626 bp, 291 bp or 258 bp RT-PCR products from the RNA encoding human β-actin, β-globin or GAPDH genes respectively. PCR Primer sequences used were; β-globin, exon I forward 5'-GGT GAA CGT GGA TGA AGT TG-3' and exon III reverse 5'-AGC ACA CAG ACC AGC ACG T-3'; β-actin, exon 1 forward 5'-CCTCGCCTTTGCC GATCC-3' and exon 4 reverse 5'-GGATCTTCATGAGGTAGTCAGTC-3'; GAPDH forward 5'-AGAAGGCTGGGGCTCATTTG-3' and reverse 5'-AGGGGCCATCCACAGTCTTC-3'.

OmniKlenTaq DNA polymerase and the recommended PEC 1 was used according to manufacturer's instructions. The mutated OmniKlenTaq DNA polymerase when used with PEC 1 has the ability to tolerate many inhibitors commonly found in biological samples. However, during these experiments it was shown that the combination of AffinityScript RT, OmniKlenTaq and PEC 1 failed to generate RT-PCR products irrespective of the blood concentration used.

During a separate evaluation and according to manufacturer's claims it was confirmed that OKT polymerase and PEC 1 were able to amplify PCR products directly from genomic DNA contained in whole blood in both liquid and freeze dried RTG formats (data not shown).

Optimising the Concentration of Blood

To determine the most appropriate blood concentration that could support a direct RT-PCR reaction a range of blood dilutions, 1.25% to 0.03% (v/v), were generated using PBS. The aim was to identify the most appropriate concentration of blood that did not exhibit any inhibition on direct RT-PCR amplification. As a control, RNA (200 ng) isolated from whole blood or purified from HeLa cells were added to the diluted blood and RT-PCR was performed using β-globin, GAPDH and β-actin primers respectively.

Blood total RNA was purchased from Clontech and HeLa cells RNA was extracted using the illustra RNAspin kit (GE Healthcare). The quality of the RNA was assessed using 2% agarose gel electrophoresis confirming the presence of the 28S, 18S and the faint 5S ribosomal RNA. RNA concentration was determined using the Nanovue spectrophotometer (GE Healthcare). Results confirmed that the RNA derived from both whole blood and HeLa cells was of sufficient quality for RT-PCR. The OmniKlenTaq and PEC-1 system used initially was replaced with a cloned version of wildtype Taq DNA polymerase (GE Healthcare) in combination with AffinityScript RT following the protocol described above.

Using this alternative RT-PCR system, direct RT-PCR products were generated (see FIG. 1). However amplicons were observed from only samples containing blood concentrations <0.06% (v/v) and to which RNA was added (FIG. 1, Lanes 11 and 13). Therefore, these data indicate that even relatively low blood concentrations contain RT-PCR inhibitors. The optimal conditions for reducing the effect of potential RT-PCR inhibitors was identified as <0.03% (v/v) blood (lane 13) when using the wildtype Taq DNA polymerase.

Similar results were observed when HeLa total RNA was added to diluted blood in combination with β-actin and GAPDH primer sets (data not shown). Based upon these results wildtype Taq DNA polymerase and AffinityScript RT was used in all subsequent liquid based RT-PCR reactions.

Optimised Cellular Lysis Using SDS and CD

The use of SDS to lyse cells followed by a treatment with cyclodextrin (CD) as a detergent sequesterant is known (Horton, J. K., 1997, In-situ cell extraction and assay method, EP 0863402 B1). Experiments were conducted to investigate if SDS and cylcodextrin could be used to disrupt cells and potentially improve the liberation and survival of RNA by denaturing and inactivating proteins and enzymes including ribonucleases (RNases), whilst at the same time not exhibiting any inhibitory effect on the direct RT-PCR amplification reaction.

Figure 2:
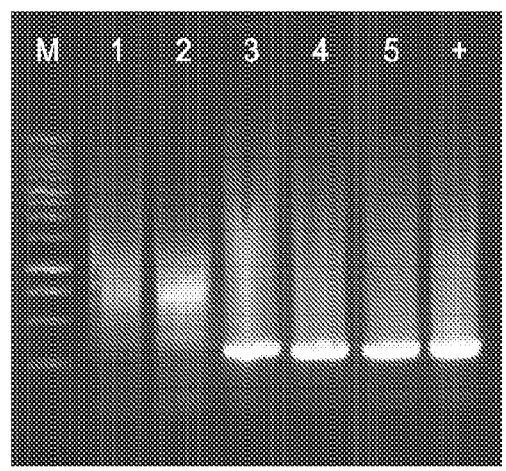
FIG. 2 shows RT-PCR products generated using 0.03% (v/v) blood supplemented with blood RNA (200 ng). These RT-PCR products are generated in the presence of differing SDS:cyclodextrin molar ratios. M—DNA markers; 1—human genomic DNA; 2—Blood plus total RNA; 3—Blood plus total RNA SDS:CD 1:1; 4—Blood plus total RNA SDS:CD 1:1.5; 5—Blood plus total RNA SDS:CD 1:2 and (+)—positive control total RNA only.

The performance of different SDS:CD ratios were compared using blood diluted with PBS to a concentration range of 1.25% to 0.03% (v/v). To represent, and as a means of illustration, the results derived from the use of 0.03% (v/v) blood is shown (FIG. 2). Cells from EDTA anti-coagulated blood were lysed by the addition of SDS to a final concentration of a 2% (w/v) and incubated at room temperature for 5 min. The SDS was neutralised by the addition of freshly prepared CD at molar ratios of SDS:CD 1:1, 1:1.5 and 1:2.

RT-PCR was performed using the β-globin specific primers. All blood samples were spiked with RNA (200 ng) derived from white blood cells. A positive control was performed using purified blood total RNA. This study was designed to optimise the ratio of SDS:CD and to determine if using the SDS and CD system had any inhibitory effect on the RT-PCR reaction.

The correct β-globin PCR product (291 bp) was generated from only those blood samples which contained the added RNA and had been subjected to the SDS and CD treatment (see FIG. 2). PCR products were not generated either in the absence of SDS which is a potent protein denaturant or when using only genomic DNA. In the absence of added RNA, samples failed to generate the RT-PCR products. Based upon these results all subsequent experiments used a SDS:CD molar ratio of 1:2. These surprising results demonstrate that the SDS:CD system can be used to significantly improve the efficacy of RT-PCR reactions.

RT-PCR Using RT-PCR RTG Beads

Due to the successful amplification of RT-PCR products using wildtype Taq DNA polymerase, the use of GE Healthcare RT-PCR RTG beads was evaluated. These beads contain the same Taq DNA polymerase used in the previous experiments but contain M-MuLV Reverse Transcriptase. These enzymes are stabilised using an excipient mixture in a freeze-dried format supplemented with all the reagents required for RT-PCR.

RT-PCR reactions were performed using SDS:cyclodextrin blood lysis system described earlier and the RT-PCR RTG beads according to manufacturer's recommendations. RT-PCR RTG beads were placed on ice and resuspended in RNase free water. EDTA anti-coagulated blood was diluted with PBS to a concentration range of 1.25% to 0.03% (v/v), total RNA (200 ng) derived from blood or HeLa cells and either oligo d(T) or random hexamers were added. Prior to use the RNA was incubated at 65° C. for 5 min then allowed to cool at room temperature for 10 minutes. To initiate the RT reaction all reagents were mixed and incubated at 42° C. for 60 minutes, followed by 95° C. for 3 minutes. PCR-primer sets for β-actin, β-globin and GAPDH was used and the following thermocycle was performed for 32 cycles at 95° C. for 30 seconds, 55° C. for 1 minute and 72° C. for 1 minutes with an extension of 72° C. for 5 minutes.

Figure 3:
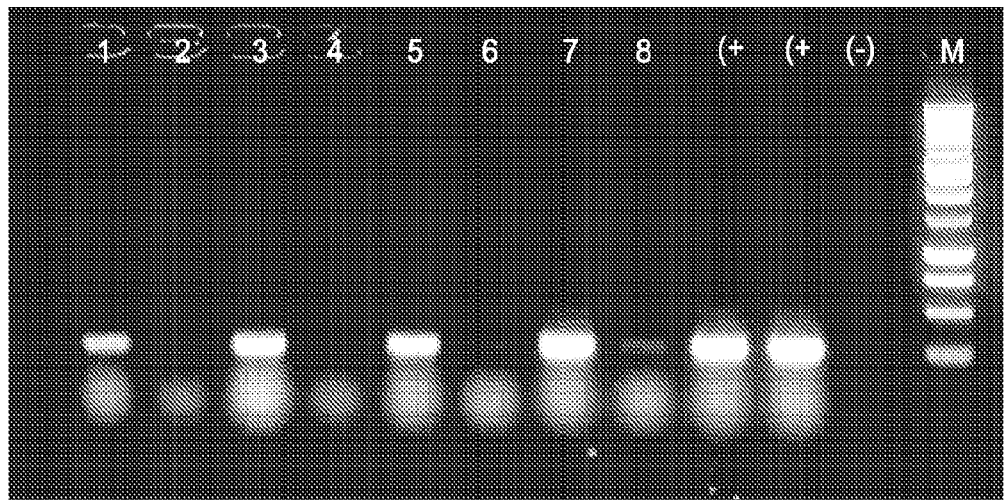
FIG. 3 shows the results of direct RT-PCR using RT-PCR RTG beads (GE Healthcare), and various concentrations of anti-coagulated blood, random hexamers and β-globin primers. 1—Blood (0.1% v/v) plus RNA (200 ng); 2—Blood (0.1% v/v); 3—Blood (0.05% v/v) plus RNA (200 ng); 4—Blood (0.05% v/v); 5—Blood (0.025% v/v) plus RNA; 6—Blood (0.025% v/v); 7—Blood (0.013% v/v) plus RNA; 8—Blood (0.013% v/v) (+)—Positive control and (−)—Negative control. RT-PCR products derived from endogenous blood RNA are visible in lanes 6 and 7.

Direct RT-PCR products were successfully generated when using RT-PCR RTG beads with random primers and oligo dT. This was in combination with diluted blood at a concentration of 0.1% (v/v) and supplemented with RNA (FIG. 3). A visual inspection of the agarose gel appears to indicate that the amount of product generated increases with decreasing blood concentrations. This implies that even at low blood dilutions [0.1% (v/v)] a degree of RT-PCR inhibition is still present, however, the use of RT-PCR RTG beads appears to overcome a portion of this inhibitory effect. Encouragingly, direct RT-PCR products were visible (albeit at low amounts) when using <0.025% (v/v) blood in the absence of added RNA (see FIG. 3, lanes 6 & 7). This indicates that the RT-PCR products are being amplified directly from the endogenous RNA present in blood. This demonstrates that the RT-PCR RTG beads system when used in combination with low blood concentrations is able to overcome the effect of some RT-PCR inhibitors present. At higher blood concentration (0.1% v/v) even in the presence of added total RNA (200 ng) RT-PCR inhibition was still apparent. Comparable results were obtained when using Hela cell RNA with GAPDH and β-actin primer.

A system was therefore identified, in which the inhibitory effect was reduced i.e. the system was capable of generating a RT-PCR product from i) 0.1% (v/v) blood in the presence of added RNA and ii) endogenous RNA from blood <0.025% (v/v). However, this amplification did appear to be sub-optimal.

Additional experiments were performed to investigate if the EDTA used to prevent the coagulation of blood was eliciting any inhibitory effect on the generation of direct RT-PCR products. EDTA is a known chelator of $Mg^{2+}$ ions, and these ions are required as a cofactor for many DNA modifying enzymes including the MMLV-RT and Taq DNA polymerase used in the RT-PCR RTG beads. The amount of $Mg^{2+}$ required is finely balanced and too much $Mg^{2+}$ will result in enhanced stabilisation of double stranded DNA therefore making the duplex more resistant to denaturation which is an important initial step in PCR. Calculations of the EDTA present in the blood used in these experiments, appeared to be negligible. The amount of EDTA used in the anti-coagulant blood tubes is 6.1 mM. At a blood concentration of 0.1% (v/v), the amount of EDTA in the blood sample would be <0.05 mM. This was considered insufficient to affect the efficiency of the RT-PCR process as the RT-PCR RTG beads contain 1.5 mM $Mg^{2+}$ ions. However, for confirmation RT-PCR reactions were set-up in which additional amounts of $MgCl_2$ (1.5, 2.5 and 3.5 mM) was added to 0.1% (v/v) blood supplemented with total RNA. On completion the samples were subjected to gel electrophoresis and results indicated that no detectable decrease in the yield of the direct RT-PCR products was observed (data not shown). Therefore it was concluded that the EDTA present in the anti-coagulation system did not cause any significant inhibition to the generation of RT-PCR products.

As an attempt to further optimise the yield of the direct RT-PCR product a literature search was conducted to identify potential sources of RT-PCR inhibition. Inhibitors in blood which have been identified are either natural components of blood, mainly haem, hematin, haemoglobin, and immunoglobulin G or added anticoagulants such as EDTA and heparin (Al-Soud and Radstrom, 2001, J Clin Micro 39, 485-493). The interaction between these inhibitors and RNA or genomic DNA prevents the binding of the polymerases to the template. A component used to reduce inhibition of PCR is bovine serum albumin (BSA), which is able to bind to haem and prevent its inhibitory action on the polymerase. BSA has been shown to enhance nucleic acid amplification in the presence of blood-derived inhibitors such as haemoglobin and lactoferrin. BSA binds to haem ($Fe^{2+}$), reducing the haem-derived inhibitory effect on the RT and DNA polymerase enzymes. Therefore the addition of BSA may reduce the observed inhibition of the RT-PCR reaction. Based upon the studies of Comey et al, 1994; J. Forensic Sci 39, 1254-1269; Al-Soud & Radstrom, 2000; J Clin Micro 39, 485-493, BSA was added to the reaction mixture over a concentration ranging from 0.6% to 1.2% (w/v).

Experiments were performed in which the blood concentration was diluted with PBS from 0.025-0.02% (v/v) and the RT-PCR RTG bead mixture was supplemented with a BSA ranging from 0-1.2% (w/v). The method was also slightly modified to include a 15 minute SDS incubation at 37° C., followed by a 5 minute room-temperature incubation with cyclodextrin. This ensures sufficient time for SDS to affect efficient cellular lysis and inhibit any RNase activity present. It will also facilitate the efficient sequestration and neutralization of SDS by cyclodextrin before the initiation of the RT-PCR reaction. Representative RT-PCR results are described in FIG. 4.

Figure 4:
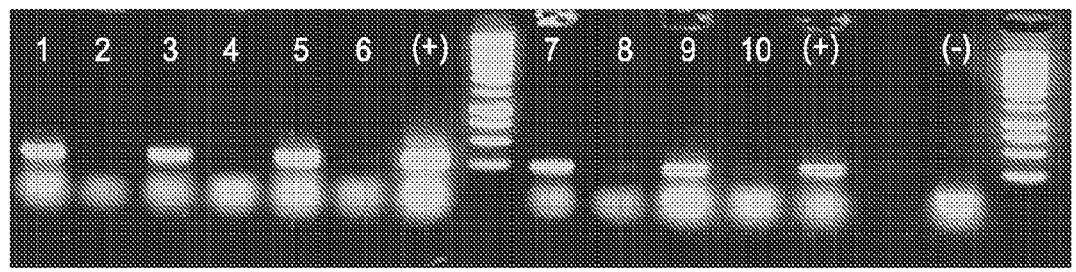
FIG. 4 shows the results of direct RT-PCR using anti-coagulated 0.1% blood (v/v). The amplicons shown were generated using RT-RTG beads, random hexamers, β-globin primers in combination with increasing amounts of BSA. Lane 1—0.1% blood, no BSA plus RNA (200 ng); 2—0.1% (v/v) blood, no BSA no RNA; 3—0.1% (v/v) blood, 0.3% (w/v) BSA plus RNA (200 ng); 4—0.1% (v/v) blood, 0.3% (w/v) BSA no RNA; 5—0.1% (v/v) blood, 0.6% (w/v) BSA plus RNA (200 ng); 6—0.1% (v/v) blood, 0.3% (w/v) BSA no RNA; 7—0.1% (v/v) blood, 0.9% (w/v) BSA plus RNA (200 ng); 8—0.1% (v/v) blood, 0.9% (w/v) BSA no RNA; 9—0.1% (v/v) blood, 1.2% (w/v) BSA plus RNA (200 ng); 10—0.1% (v/v) blood, 1.2% (w/v) BSA no RNA; M—DNA molecular weight markers, (+) and (−) positive and negative controls respectively. RT-PCR products are generated in the absence of added RNA (see lanes 4, 6, 8 & 10).
Figure 5A:
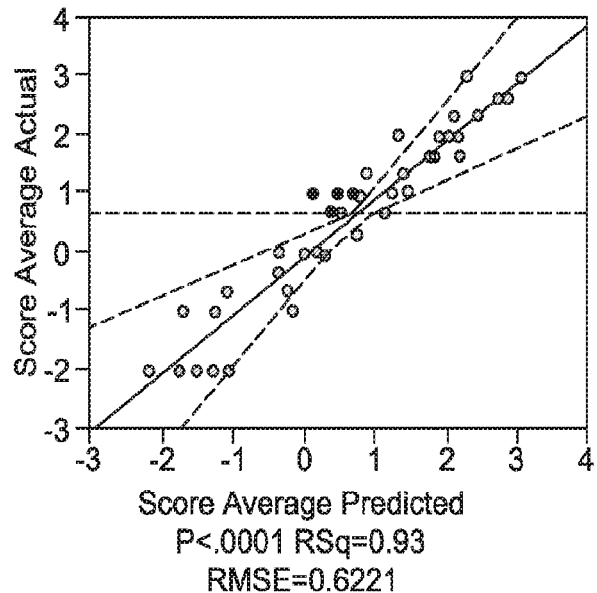
FIGS. 5 to 8 show graphs of actual versus predicted values to demonstrate $R^2$ (reflecting correlation), and results from Prediction Profiler.
Figure 5B:
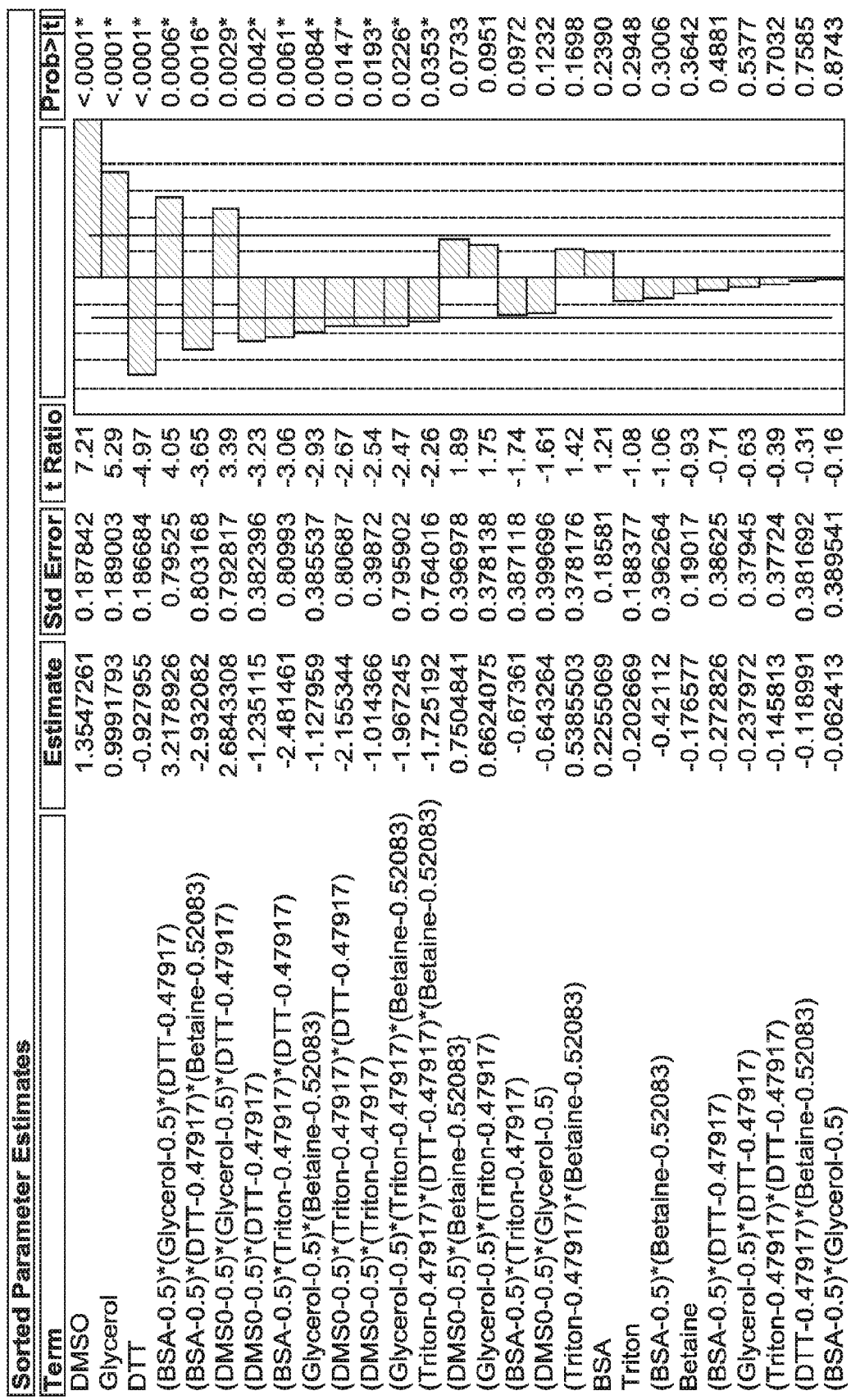
Figure 5C:
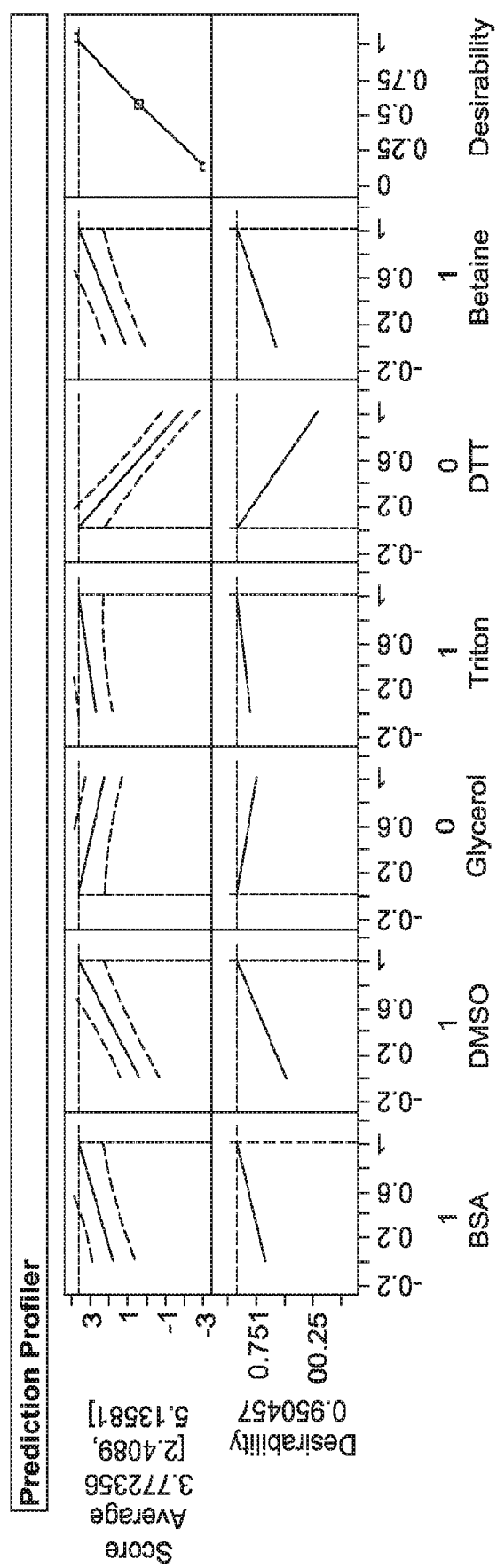
Figure 6A:
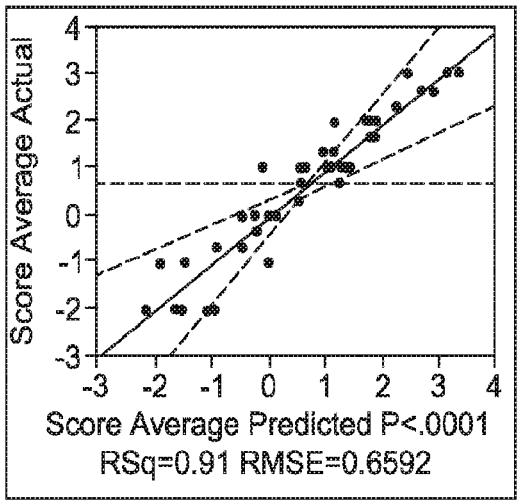
Figure 6A:
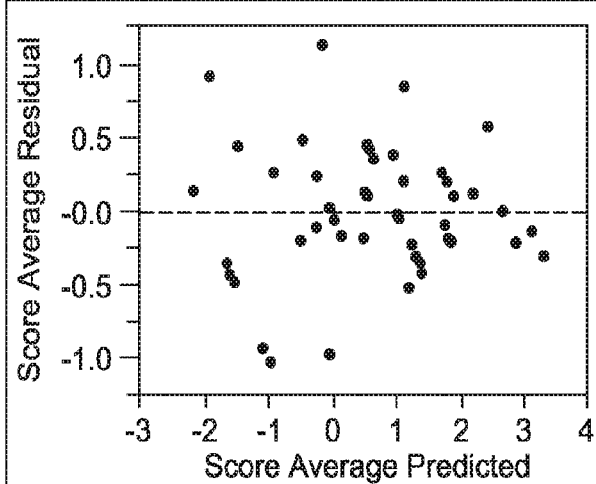
Figure 6C:
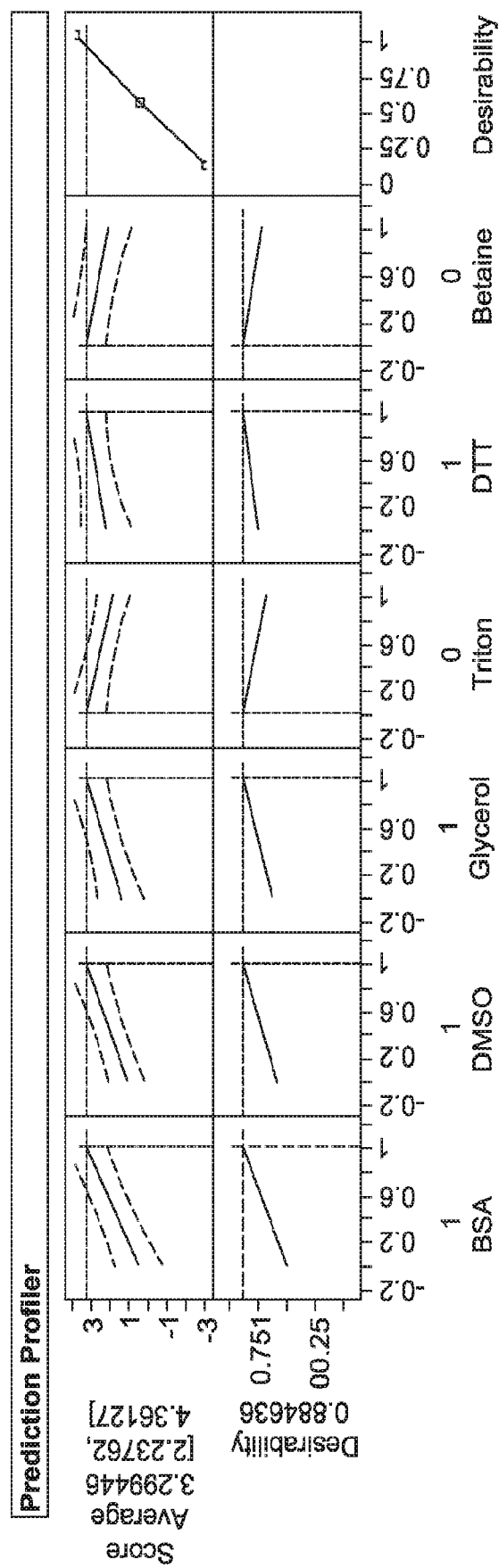
Figure 7A:
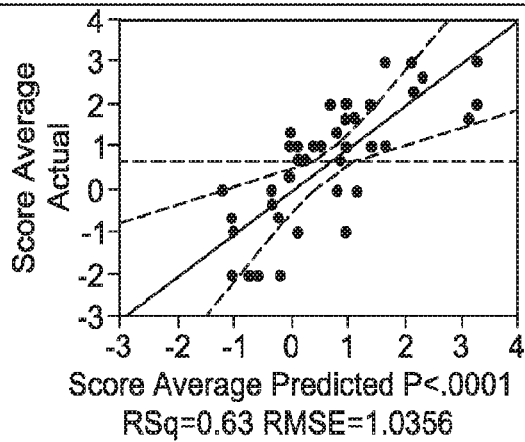
Figure 7A:
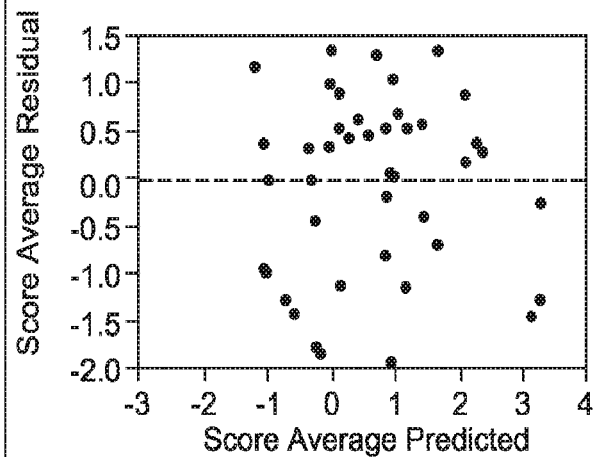
Figure 7B:
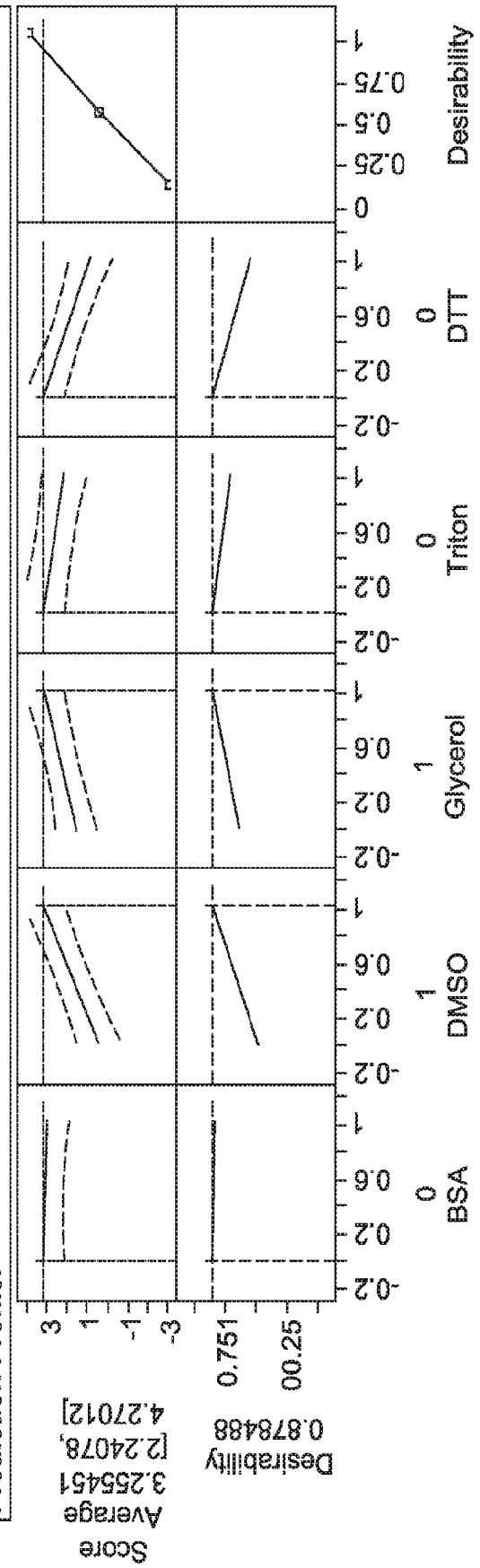
Figure 8:
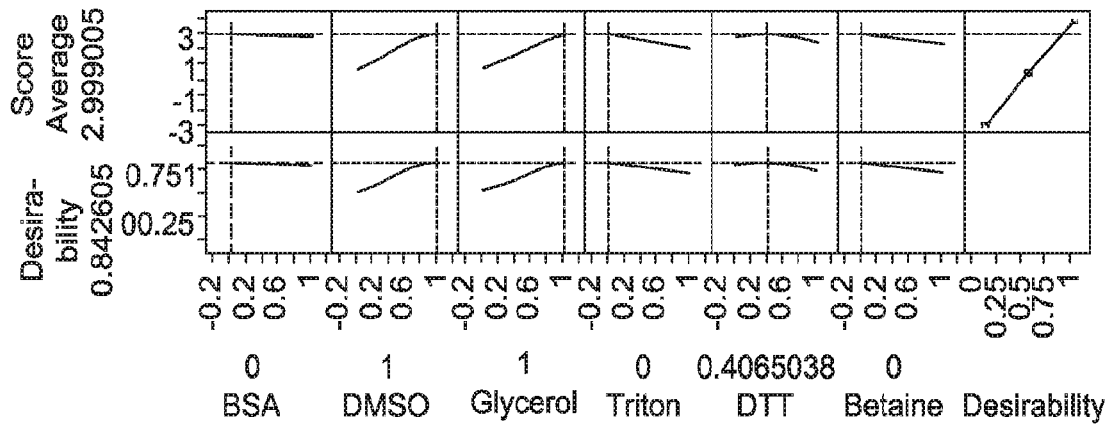

Direct RT-PCR amplicons were generated in reactions initiated in the absence of any added total RNA (see FIG. 4; lanes 4, 6, 8 and 10). Gel electrophoresis results indicate that the addition of BSA >0.6% (w/v) supported the generation of a direct RT-PCR products. However, at elevated concentrations of BSA [1.2% (w/v)] a precipitation in the RT-PCR reaction mixture was noted. Comparable results were obtain, using the GAPDH and β-actin primer in the absence of added total RNA. A summary of the results are described in Table 1. Based upon these experiments it was concluded that optimal conditions for generating direct RT-PCR products using the RT-PCR RTG beads were 0.3% and 0.6% (w/v) BSA supplements in combination with 0.075% and 0.1% (v/v) blood respectively.

| Diluted Blood | Added BSA % (w/v) | | | | |
|---|---|---|---|---|---|
| % (v/v) | 0% | 0.3% | 0.6% | 0.9% | 1.2%* |
| 0.25% | − | + | + | − | − |
| 0.5% | − | + | ++ | + | − |
| 0.75% | − | ++ | ++ | + | − |
| 0.1% | − | + | ++ | ++ | ++ |
| 0.2% | − | − | + | + | − |

Table 1. Summary of direct RT-PCR results performed in the absence of added total RNA using RT-PCR RTG beads supplemented with increasing amounts of BSA. No visible amplicons observed (−), (+) and (++) indicate the successful generation of increasing amounts of direct RT-PCR products. * precipitation was observed in the reaction tube.

Formal Design of Experiment—Investigating the Effect of Added Chemicals on the Performance of Direct RT-PCR Using RT-PCR RTG Beads As an attempt to further increase the amount of direct RT-PCR product using the RT-PCR RTG beads a number of nucleic acid amplification enhancers were identified. Their ability to increase RT-PCR product yield was investigated by performing a formal statistical Design of Experiment. To achieve this it was decided to use the combination of RT-PCR RTG beads supplemented with 0.6% (w/v) BSA with 0.1% (v/v) blood diluted with PBS a the model system from which to develop more enabling reaction mixtures.

Six chemicals considered to enhance PCR or RT-PCR reactions were selected for a formal Design of Experiment (DOE). These components included BSA, glycerol, Dimethyl sulfoxide (DMSO), Triton X-100, DTT and betaine.

Addition of BSA has been shown to enhance nucleic acid amplification in the presence of blood-derived inhibitors such as haemoglobin and lactoferrin (Comey et al, 1994; J. Forensic Sci 39, 1254-1269; Al-Soud & Radstrom, 2000; J Clin Micro 39, 485-493). BSA binds to haem ($Fe^{2+}$), reducing the haem-derived inhibitory effect on reverse transcriptase and DNA polymerase enzymes.

DMSO is a polar solvent that dissolves both polar and non-polar compounds, therefore addition of DMSO promotes the solubilization of the reaction components in the presence of elevated BSA concentrations. DMSO is used as an enhancing agent and is included as part of a standard optimization of PCR amplifications (Varadaraj and Skinner, 1994; Gene, 140, 1-5). DSMO can also increase amplification specificity by destabilizing non-specific primer binding. Addition of 1-10% DMSO has been reported to increase the yield of PCR products by lowering annealing temperature thereby promoting primer binding and to disrupt regions of nucleic acid secondary structure [Simonovic et al, 2012; Arch. Bio. Sci (Belgrade) 64, 865-876].

The addition of glycerol (e.g. 5-20%) destabilizes nucleic acid duplexes and disrupts RNA secondary structure. The addition of glycerol to a PCR mixture is reported to increase the thermal stability of the polymerase and decreases the denaturation temperature necessary for duplex strand separation (Cheng et al, 1994; PNAS 91 5695-5699).

Triton X-100 (and Brij 56 or 58) are non-ionic detergents, which can be used in PCR (e.g. up to 0.5%) to reduce DNA polymerases from associating or sticking to themselves or to the walls of the reaction tube. Triton X-100 can stabilize Taq DNA polymerase at elevated temperatures, aid solubilizing reaction components in the presence of elevated BSA concentrations and destabilizes nucleic acid secondary structures (Gelfand and White, 1990; Thermostable DNA polymerases pp 129-141 in PCR Protocols (Innis, Gelfand, Sinisky & White eds; Academic Press NY).

Dithiothreitol (DTT) and tris(2-carboxyethyl)phosphine (TCEP) are reducing agents which have been reported to denature and prevent the formation of RNA secondary structure. DTT is used at ~5 mM in PCR buffers to help maintain the active conformational structure of the thermostable DNA polymerase (Van Pelt-Verkuil et al, 2008; Principles and Technical Aspects of PCR amplification). TCEP is a derivative of DTT that has been shown to increase RNA stabilisation and is reported to be more resistant to oxidation (Rhee and Burke, 2004; Anal Biochem 325, 137-143).

The addition of betaine (~1M) has been reported to improve nucleic acid amplification by reducing the formation of secondary structure in GC-rich regions (Rees et al, 1993 Biochem 32, 137-144 and Hencke et al, 1997; NAR 25, 3957-3958). DMSO is thought to aid nucleic acid amplification in a similar manner by interfering with hydrogen bond formation between the DNA duplex (Geiduschek and Herskovits, 1961; Arch Biochem Biophys, 95, 114-129).

A total of 48 experiments were performed during the DOE, investigating the effect of these chemicals on the performance of direct RT-PCR reactions. The experiments were performed using specific combination of these chemicals as defined in the DOE by the statistical SAS JMP software. These specific combinations were added to RT-PCR RTG beads to assess nucleic acid amplification. The DOE was designed to investigate the main effects of each individual chemical but also their $2^{nd}$ and $3^{rd}$ order interactions with the other chemicals.

An initial set of experiments were performed that identified an appropriate concentration or blood (0.1% v/v) and BSA (0.6% w/v) for use in DOE experiments. Additional experiments developed an efficient cellular lysis system using SDS and cyclodextrin and indicated that. EDTA (at the concentration used) did not exhibit any inhibitory effects on the direct RT-PCR reaction. Individual experiments from the DOE were performed using a final blood concentration of 0.1% (v/v) and BSA 0.6% (w/v). All reactions were performed in triplicate.

Cells from EDTA anti-coagulated blood were lysed by the addition of SDS [final concentration of a 2% (w/v)] and incubated at room temperature, for 15 min. The SDS was removed by the addition of freshly prepared cyclodextrin at a molar ratio of SDS:cyclodextrin 1:2 followed by a 5 minute room-temperature incubation. The mixture was then subjected to RT-PCR using RT-PCR RTG beads supplemented with combinations of chemicals as defined in the DOE (see Table 2). Direct RT-PCR reactions were performed as described earlier and RT-PCR products were subjected to agarose gel electrophoresis. A successful amplification was determined by the presence of a single PCR product of 291 bp for human β-globin (data not shown). To determine any improvement, the band intensity was compared to the 'standard' control reaction [0.1% blood using RT-PCR RTG beads supplemented with 0.6% (v/v) BSA]. Analysis was scored by visual inspection, with each reaction being given a score between −3 and +3 as a comparison to the 'standard', with +3 reflecting a significantly higher product yield and −3 a significantly lower product yield than the 'standard' reaction. Results are presented in Table 2.

The chemical combinations that generated a score >7 were considered indicative of an improved direct RT-PCR product yield. These are summarised in Table 3. However to ensure that no alternative combinations were missed i.e. those that were not performed as part of the DOE (Table 2), statistical models were generated based upon the DOE results (see FIGS. 5, 6, 7 & 8). To indicate the efficacy of the DOE approach, the chemical composition of reaction 30 was equivalent to that of the control and during the "blind scoring", reaction 30 was scored the same as the control i.e., zero.

| Reaction mix | BSA 1% (w/v) | DMSO 5% (v/v) | Glycerol 10% (v/v) | Triton 0.5% (v/v) | DTT (10 mM) | Betaine (1 M) | Score 1 | Score 2 | Score 3 | Total |
|---|---|---|---|---|---|---|---|---|---|---|
| 1 | 1 | 0 | 1 | 0 | 1 | 0 | 2 | 2 | 2 | 6 |
| 2 | 0 | 1 | 0 | 0 | 1 | 1 | 1 | 1 | 2 | 4 |
| 3 | 0 | 1 | 1 | 0 | 0 | 0 | 3 | 3 | 3 | 9 |
| 4 | 1 | 0 | 0 | 0 | 1 | 0 | 0 | 0 | 0 | 0 |
| 5 | 1 | 1 | 0 | 0 | 0 | 1 | 3 | 2 | 3 | 8 |
| 6 | 0 | 1 | 1 | 1 | 1 | 1 | 1 | 0 | 0 | 1 |
| 7 | 0 | 0 | 1 | 0 | 1 | 1 | −1 | −1 | 0 | −2 |
| 8 | 1 | 1 | 1 | 0 | 0 | 1 | 2 | 2 | 2 | 6 |
| 9 | 1 | 1 | 0 | 0 | 0 | 0 | 2 | 3 | 3 | 8 |
| 10 | 1 | 0 | 1 | 0 | 0 | 0 | 1 | 1 | 1 | 3 |

-continued

| Reaction mix | BSA 1% (w/v) | DMSO 5% (v/v) | Glycerol 10% (v/v) | Triton 0.5% (v/v) | DTT (10 mM) | Betaine (1 M) | Score 1 | Score 2 | Score 3 | Total |
|---|---|---|---|---|---|---|---|---|---|---|
| 11 | 1 | 1 | 1 | 1 | 0 | 1 | 2 | 3 | 2 | 7 |
| 12 | 1 | 0 | 0 | 0 | 0 | 0 | 0 | 0 | 0 | 0 |
| 13 | 1 | 1 | 1 | 0 | 1 | 0 | 3 | 3 | 3 | 9 |
| 14 | 0 | 1 | 0 | 0 | 1 | 0 | 0 | 0 | 0 | 0 |
| 15 | 0 | 1 | 0 | 1 | 1 | 0 | 2 | 1 | 1 | 4 |
| 16 | 0 | 0 | 1 | 1 | 0 | 0 | 1 | 2 | 2 | 5 |
| 17 | 1 | 0 | 0 | 0 | 0 | 1 | −1 | 0 | 0 | −1 |
| 18 | 0 | 1 | 0 | 0 | 0 | 0 | 3 | 3 | 3 | 9 |
| 19 | 0 | 0 | 1 | 0 | 1 | 1 | 1 | 1 | 1 | 3 |
| 20 | 1 | 1 | 0 | 0 | 1 | 1 | 1 | 1 | 1 | 3 |
| 21 | 1 | 0 | 1 | 1 | 1 | 0 | 3 | 2 | 2 | 7 |
| 22 | 0 | 0 | 1 | 1 | 1 | 1 | 1 | 1 | 0 | 2 |
| 23 | 1 | 0 | 1 | 0 | 0 | 1 | 0 | 2 | 1 | 3 |
| 24 | 1 | 0 | 1 | 1 | 0 | 1 | 0 | 1 | 1 | 2 |
| 25 | 0 | 1 | 0 | 1 | 1 | 0 | −2 | −2 | −2 | −6 |
| 26 | 0 | 0 | 0 | 0 | 0 | 1 | −2 | −2 | −2 | −6 |
| 27 | 1 | 0 | 0 | 1 | 1 | 1 | −2 | −2 | −2 | −6 |
| 28 | 0 | 1 | 0 | 0 | 0 | 1 | 1 | 1 | 1 | 3 |
| 29 | 0 | 0 | 0 | 1 | 1 | 0 | 2 | 0 | 1 | 3 |
| 30 | 0 | 0 | 0 | 0 | 0 | 0 | 0 | 0 | 0 | 0 |
| 31 | 0 | 0 | 1 | 0 | 1 | 0 | −2 | 2− | −2 | −6 |
| 32 | 1 | 0 | 0 | 1 | 0 | 1 | 0 | 1 | 1 | 2 |
| 33 | 0 | 0 | 1 | 1 | 0 | 1 | 1 | 1 | 1 | 3 |
| 34 | 0 | 0 | 1 | 0 | 0 | 1 | 1 | 1 | 1 | 3 |
| 35 | 1 | 1 | 1 | 1 | 0 | 0 | 2 | 2 | 3 | 7 |
| 36 | 0 | 0 | 0 | 0 | 1 | 1 | 0 | 0 | 0 | 0 |
| 37 | 1 | 0 | 1 | 0 | 1 | 1 | −1 | −1 | −1 | −3 |
| 38 | 0 | 0 | 0 | 1 | 0 | 0 | −2 | −2 | −2 | −6 |
| 39 | 1 | 1 | 0 | 1 | 1 | 1 | −1 | −1 | −1 | −3 |
| 40 | 1 | 1 | 0 | 1 | 1 | 0 | −2 | −2 | −2 | −6 |
| 41 | 1 | 1 | 1 | 1 | 1 | 1 | 0 | 0 | 0 | 0 |
| 42 | 1 | 1 | 0 | 1 | 0 | 1 | 3 | 2 | 2 | 7 |
| 43 | 0 | 1 | 1 | 0 | 0 | 1 | 2 | 2 | 2 | 6 |
| 44 | 1 | 0 | 0 | 1 | 0 | 0 | −1 | −1 | −1 | −3 |
| 45 | 1 | 1 | 0 | 1 | 0 | 0 | 1 | 1 | 1 | 3 |
| 46 | 0 | 1 | 1 | 1 | 0 | 0 | 3 | 3 | 2 | 7 |
| 47 | 0 | 0 | 0 | 1 | 1 | 1 | 1 | 1 | 1 | 3 |
| 48 | 1 | 1 | 1 | 1 | 1 | 0 | 1 | 2 | 2 | 5 |

Table 2—Chemical components in the Design of Experiment reactions. The presence and absence of chemicals in the DOE reactions are indicated by (1) and (0) respectively. For BSA (1) and (0) indicates 1% or 0.6% (w/v) respectively. Scores were determined by the visual inspection of RT-PCR product yield compared to that generated for the control reaction containing only BSA 0.6% (w/v). A score of +3 or −3 indicates a significantly greater or lower RT-PCR product yield compared to the control reaction.

TABLE 3

DOE chemical combinations that scored ≥7 (max possible = 9) compared to the control reactions during direct RT-PCR reactions.

| Reaction | Chemical combination | score |
|---|---|---|
| 3 | BSA 0.6% (w/v), DMSO 5% (v/v) & Glycerol 10% (v/v) | 9 |
| 5 | BSA 1.0% (w/v), DMSO 5% (v/v) & Betaine (1M) | 8 |
| 9 | BSA 1.0% (w/v) & DMSO 5% (v/v) | 8 |
| 11 | BSA 1.0% (w/v), DMSO 5% (v/v), Glycerol 10% (v/v), Triton 0.5% (v/v) & Betaine (1M) | 7 |
| 13 | BSA 1% (w/v), DMSO 5% (v/v), Glycerol 10% (v/v) & DTT (10 mM) | 9 |
| 18 | BSA 0.6% (w/v) & DMSO 5% (v/v). | 9 |
| 21 | BSA 1.0% (w/v), Glycerol 10% (v/v), Triton 0.5% (v/v) & DTT (10 mM) | 7 |
| 35 | BSA 1.0% (w/v), DMSO 5% (v/v), Glycerol 10% (v/v) & Triton 0.5% (v/v) | 7 |

TABLE 3-continued

DOE chemical combinations that scored ≥7 (max possible = 9) compared to the control reactions during direct RT-PCR reactions.

| Reaction | Chemical combination | score |
|---|---|---|
| 42 | BSA 1.0% (w/v), DMSO 5% (v/v), Triton 0.5% (v/v) & Betaine (1M) | 7 |
| 46 | BSA 0.6% (w/v), DMSO 5% (v/v), Glycerol 10% (v/v), & Triton 0.5% (v/v) | 7 |

Models Based Upon Results From the Design of Experiment

Analysis of the DOE results was performed (see Table 2) to determine the optimum combination of components that would give the highest score (reflecting RT-PCR product yield based on band intensity). Using the SAS-JMP software and the associated Prediction Profiler software, statistical models were generated describing the mixture of components that gave the highest scores and therefore the highest RT-PCR product yield. The following models were identified.

1. BSA 1% (w/v), DMSO 5% (v/v), Triton X-100 0.5% (v/v) and betaine (1 M) (average score of 3.77) ($R^2$=0.93). This model was performed as DOE reaction 42.

2. BSA 1% (w/v), DMSO 5% (v/v), glycerol 10% (v/v) and DTT (10 mM) (average score of 3.29) ($R^2$=0.91). This model was performed as DOE reaction 13.
3. BSA 0.6% (w/v), DMSO 5% (v/v) and glycerol 10% (v/v) (average score of 3.26) ($R^2$=0.63). This model was performed as DOE reaction 3.
4. BSA 0.6% (w/v), DMSO 5% (v/v), Glycerol 10% (v/v) and DTT 4.1 mM (average score of 3.00; $R^2$=0.58). This combination of chemicals were identified based upon the statistical model only and not as a direct result of the DOE. This combination of chemicals is identical to those used in reaction mixture 13 but the BSA and DTT are at different concentrations i.e. 0.6% (w/v) and 4.1 mM versus 1% (w/v) and 10 mM as defined in reaction 13 respectively.

The scores and $R^2$ values were generated using Prediction Profiler. $R^2$ values reflect the correlation between the actual experimentally derived scores and those predicted by the models. High $R^2$ values indicate good correlation and therefore the model exhibits a high predictive value. Graphs of actual versus predicted values to demonstrate $R^2$ (reflecting correlation), and results from Prediction Profiler are described in (see FIGS. 5, 6, 7 & 8).

Figure 9:
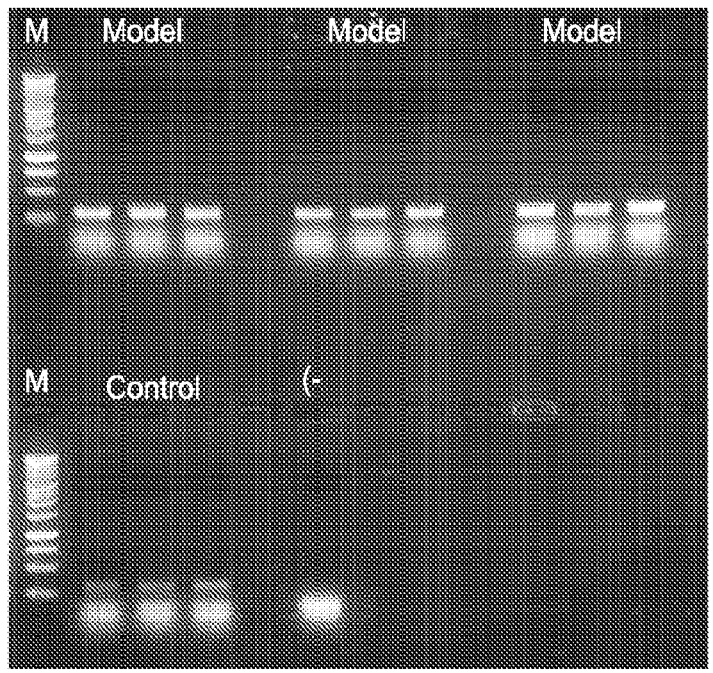
FIG. 9 shows the results of a performance validation of statistical models 1, 2 & 3. Representative agarose gels show the yield of RT-PCR products generated from the addition of the specific combinations of chemical to the RT-PCR RTG beads. These combinations were identified by Prediction-Profiler using the SAS JMP software. Model 1—BSA 1.0% (w/v), DMSO 5% (v/v), Triton 0.5% (v/v) & Betaine (1 M); Model 2—BSA 1% (w/v), DMSO 5% (v/v), glycerol 10% (v/v) and DTT (10 mM), Model 3—BSA 0.6% (w/v), DMSO 5% (v/v) and glycerol 10% (v/v), Control—BSA 0.6% (w/v), M=DNA molecular weight markers and (−) negative RT-PCR control.
Figure 10:
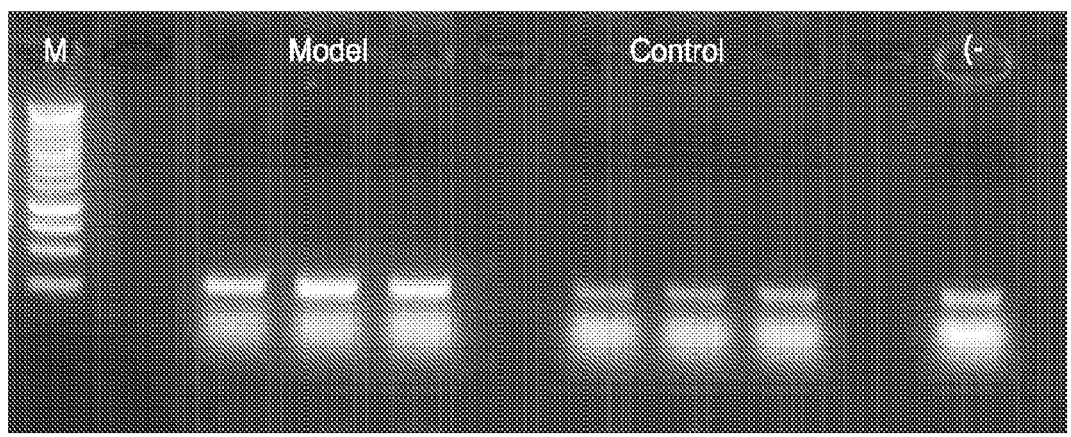
FIG. 10 shows the results of a performance validation of statistical model 4. Representative agarose gels show the yield of the RT-PCR product generated from the addition of the specific combinations of chemicals as defined in Model 4 to the RT-PCR RTG beads. This combination was identified by Prediction Profiler using the SAS JMP software. Model 4—BSA 0.6% (w/v), DMSO 5% (v/v), glycerol 10% (v/v) and DTT (4.1 mM), Control—BSA 0.6% (w/v), M=DNA molecular weight markers and (−) negative RT-PCR control.

To validate these models, confirmatory RT-PCR reactions were performed containing the predicted chemical components as described for each model. Direct RT-PCR was performed using 0.1% (v/v) blood, RT-PCR RTG beads, random hexamers and β-globin primers as described previously. The results are shown in FIGS. 9 and 10 and confirm the predictive performances of each model. The addition of the different chemicals components to the appropriate direct RT-PCR reactions generated an increase in product yield compared to that of the control system.

Model 1—BSA 1% (w/v), DMSO 5% (v/v), Triton X-100 0.5% (v/v) and betaine (1 M)
Model 2—BSA 1% (w/v), DMSO 5% (v/v), glycerol 10% (v/v) and DTT (10 mM)
Model 3—BSA 0.6% (w/v), DMSO 5% (v/v) and glycerol 10% (v/v)
Model 4—BSA 0.6% (w/v), DMSO 5% (v/v), glycerol 10% (v/v) and DTT 4 mM
Control—BSA 0.6% (w/v)

Table 4 lists three groups of chemical combinations from the DOE results and statistical models. Group 1 contains at least BSA, DMSO and glycerol; Group 2 contains at least BSA and DMSO; and Group 3 contains at least BSA and glycerol.

TABLE 4

Classification of the combination of chemical additives used to supplement and improve the performance of direct RT-PCR beads into specific Groups. The improved performance of these combinations were demonstrated either in the DOE or via validating statistical models. Group 1 contains at least BSA, DMSO and glycerol; Group 2 contains at least BSA and DMSO; and Group 3 contains at least BSA and glycerol.

| DOE Reaction | Chemical combination | Group |
|---|---|---|
| 3 | BSA 0.6% (w/v), DMSO 5% (v/v) & Glycerol 10% (v/v) - Model 3 | 1 |
| 11 | BSA 1.0% (w/v), DMSO 5% (v/v), Glycerol 10% (v/v), Triton (0.5% v/v) & Betaine (1M) | 1 |
| 13 | BSA 1% (w/v), DMSO 5% (v/v), Glycerol 10% (v/v) & DTT (10 mM) - Model 2 | 1 |
| 35 | BSA 1.0% (w/v), DMSO 5% (v/v), Glycerol 10% (v/v) & Triton (0.5% v/v) | 1 |

TABLE 4-continued

Classification of the combination of chemical additives used to supplement and improve the performance of direct RT-PCR beads into specific Groups. The improved performance of these combinations were demonstrated either in the DOE or via validating statistical models. Group 1 contains at least BSA, DMSO and glycerol; Group 2 contains at least BSA and DMSO; and Group 3 contains at least BSA and glycerol.

| DOE Reaction | Chemical combination | Group |
|---|---|---|
| 46 | BSA 0.6% (w/v), DMSO 5% (v/v), Glycerol 10% (v/v), & Triton (0.5% v/v) | 1 |
| n/a | BSA 0.6% (w/v), DMSO 5% (v/v), Glycerol 10% (v/v) and DTT 4.1 mM - Model 4 | 1 |
| 5 | BSA 1.0% (w/v), DMSO 5% (v/v) & Betaine (1M) | 2 |
| 9 | BSA 1.0% (w/v) & DMSO 5% (v/v) | 2 |
| 18 | BSA 0.6% (w/v) & DMSO 5% (v/v). | 2 |
| 42 | BSA 1.0% (w/v), DMSO 5% (v/v), Triton 0.5% (v/v) & Betaine (1M) - Model 1 | 2 |
| 21 | BSA 1.0% (w/v), Glycerol 10% (v/v), Triton 0.5% (v/v) & DTT (10 mM) | 3 |

Direct Amplification of RNA Using RT-PCR RTG Beads; Use of FTA Sample Collection Cards Paper-based sample collection cards are a popular method of storing blood and other biological tissues due to their inherent properties of providing long term stability to nucleic acids and their ease of use in many molecular biology-based workflows. These cards are impregnated with various chemicals some of which are known to inhibit enzymatic reactions especially those involved in the amplification of nucleic acids such as PCR, RT-PCR etc. To overcome this challenge, several commercially available genetically engineered DNA polymerases have been developed, including Omniklentaq and Phusion. These enzymes have been engineered to amplify genomic DNA from complex biological samples. These samples often contain multiple PCR and nucleic acid amplification inhibitors. An alternative approach is exemplified by the generation of short tandem repeat (STR) profiles for Forensic human identification purposes. These approaches, utilise especially developed buffers and protocols that reduce inhibition effects. To date no comparable solutions have been reported for the direct amplification of RNA from chemically impregnated sample collection cards.

FTA sample collection cards (GE Healthcare) are examples of chemically-coated cards. Biological samples such as blood, saliva etc. are simply applied to the cards and the impregnated chemicals inactivate micro-organism, lyse cells, denature proteins and provide long term stability to nucleic acids. These cards are commonly used in direct nucleic acid amplification workflows in which no prior nucleic acid extraction and purification steps are needed. Small punches containing the biological sample are simply excised from the FTA cards and added directly to the amplification reaction. The resultant mixture of punch and reaction buffer is subjected to PCR.

RNA can be extracted from FTA cards using RNA extraction kits such as the Illustra RNAspin kit (GE Healthcare). In the associated workflow the cards are simply treated as tissue and homogenised using a 20 gauge needle. The resultant homogenate is then transferred to the RNAspin column for the subsequent purification of RNA according the manufacturer's instructions. Based upon this finding, a study was performed to evaluate if RNA in a biological sample when applied to FTA cards could be amplified directly using the workflow and RT-PCR buffers as described earlier.

HeLa cells in PBS were applied to FTA sample collection cards. The cards were allowed to dry for 3 hours prior to the removal of a small section of the card which contained lysed HeLa cellular debris. This was accomplished using a Harris 1.2 mm diameter extraction punch. The small excised disc was subjected to the workflow previously described in which RNA was amplified directly from diluted blood. Briefly, the 1.2 mm punch was subject to a 15 minute SDS 2% (w/v) incubation at 37° C., followed by a 5 minute room-temperature incubation with a SDS:cyclodextrin molar ratio of 1:2, followed by an incubation of 65° C. for 10 min. The mixture plus punch was allowed to cool and added to RT-PCR RTG beads that were supplemented with i) β-actin RT-PCR primers, ii) the direct RT-PCR chemical additives described earlier (see Tables 3 & 4) and iii) random hexamers.

The thermocycle used was as follows; to initiate the RT reaction the punch and reagents were thoroughly mixed and incubated at 42° C. for 60 minutes, followed by PCR, involving 95° C. for 3 minutes and the following thermocycle; 40 cycles at 95° C. for 30 seconds, 55° C. for 1 minute and 72° C. for 1 minute with an extension of 72° C. for 5 minutes.

Figure 11:
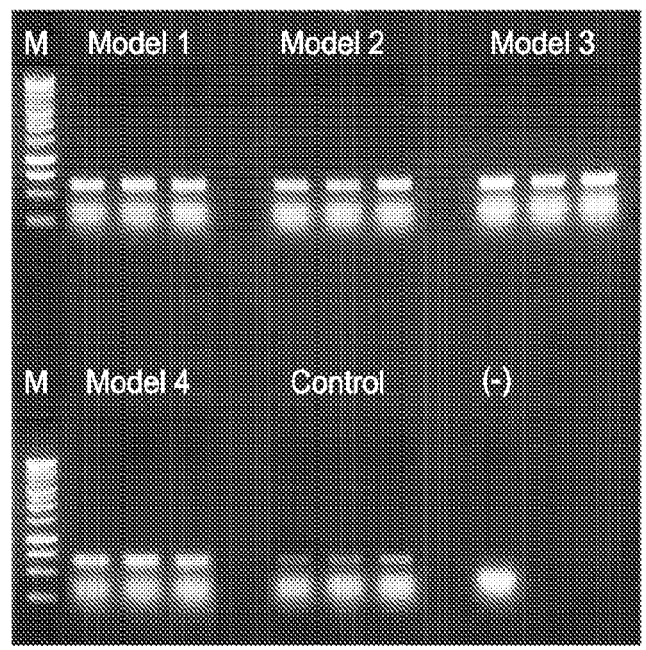
FIG. 11 shows a representative gel showing the yield of β-actin RT-PCR products (626 bp) derived from HeLa cells applied to FTA sample collection cards using RT-PCR RTG beads supplemented with specific combinations of chemicals. These combinations were identified by the Prediction-Profiler using the SAS JMP software during the DOE evaluating. Model 1—BSA 1.0% (w/v), DMSO 5% (v/v), Triton 0.5% (v/v) & Betaine (1 M), Model 2—BSA 1% (w/v), DMSO 5% (v/v), glycerol 10% (v/v) and DTT (10 mM), Model 3—BSA 0.6% (w/v), DMSO 5% (v/v) and glycerol 10% (v/v) Model 4—BSA 0.6% (w/v), DMSO 5% (v/v), Glycerol 10% (v/v) and DTT 4.1 mM, Control—BSA 0.6% (w/v), M=DNA molecular weight markers and (−) negative RT-PCR control. Increased RT-PCR product yield was observed from all reactions supplemented with the chemical additives as described in Tables 3 & 4.

RT-PCR amplicons for β-actin of the correct 626 bp size were generated in all the RT-PCR reactions. The relative yield of each RT-PCR product was determined by the intensity of bands visualised on agarose gels. The yield of RT-PCR products associated with the reactions supplemented with the chemical additives were all greater than that derived from the control reaction supplemented with BSA (0.6% w/v) only. A representative agarose gel (FIG. 11) showing the results from Model 1, Model 2, Model 3 and Model 4 compared to the control reaction is shown by way of illustration. Increased β-actin RT-PCR product yield was also observed from all RT-PCR RTG bead reactions supplemented with all the chemical additives described in Tables 3 & 4 (data not shown).

Direct Amplification of RNA by RT-PCR Reactions in a Liquid Format; Use of Diluted Blood and HeLa Cell Applied to FTA Sample Collection Cards The chemical combinations identified in both the actual DOE experiments and the statistical models are described in Tables 3 & 4. These chemical combinations were used to supplement liquid based direct RT-PCR reactions.

Figure 12:
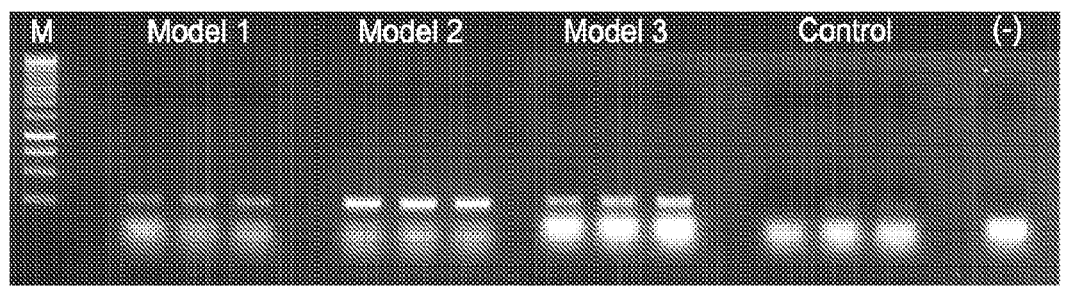
FIG. 12 shows a representative composite agarose gel showing the yield of β-globin RT-PCR products generated using diluted blood in combination with the addition of the specific chemicals to "liquid" RT-PCR reactions. These chemical combinations were identified by the Prediction-Profiler using the SAS JMP software and during the DOE evaluating the use of RT-PCR RTG beads. Model 1—BSA 0.6% (w/v), DMSO 5% (v/v) and glycerol 10% (v/v); Model 2—BSA 1% (w/v), DMSO 5% (v/v), glycerol 10% (v/v) and DTT (10 mM); Model 3—BSA 0.6% (w/v), DMSO 5% (v/v) and glycerol 10% (v/v), Control—BSA 0.6% (w/v), M=DNA molecular weight markers and (−) negative RT-PCR control.

The reaction mixture consisted of EDTA anti-coagulated human blood diluted to 0.1% (v/v) with PBS. Briefly, the diluted blood was subject to a 15 minute 2% SDS (w/v) incubation at 37° C., followed by a 5 minute room-temperature incubation with a 1:2 molar ratio of SDS:cyclodextrin, followed by an incubation of 65° C. for 10 min. The mixture was allowed to cool and then subjected to direct RT-PCR as previously described using AffinityScript RT in combination with Taq DNA polymerase. The reaction was supplemented with i) β-globin specific RT-PCR primers; exon I forward 5'-GGT GAA CGT GGA TGA AGT TG-3' and exon III reverse 5'-AGC ACA CAG ACC AGC ACG T-3'; RT-PCR product size 291 bp ii) the direct RT-PCR chemical additives described in Table 3 & 4 and iii) random hexamers. The thermocycle used was as follows; to initiate the RT reaction the diluted blood and reagents were thoroughly mixed and incubated at 42° C. for 60 minutes, followed by the addition of Taq DNA polymerase, ×10 PCR buffer etc. PCR involved heating for 95° C. for 3 minutes and the following thermocycle; 40 cycles at 95° C. for 30 seconds, 55° C. for 1 minute and 72° C. for 1 minute with an extension of 72° C. for 5 minutes.

β-globin specific amplicons of the correct size were generated in all the RT-PCR reactions (FIG. 12). A representative composite agarose gel showing the results from Model 1, Model 2, Model 3 and Model 4 compared to the control reaction is shown as way of illustration. The relative yield of each RT-PCR product was determined by the intensity of bands visualised on agarose gels and compared to that derived from control RT-PCR reaction containing 0.6% (w/v) BSA only. The yield of RT-PCR products associated with the chemical additives were all greater than that derived from the control reaction. Similar results were obtained when the other chemical additives also described in Tables 3 & 4 were used (data not shown).

Direct RT-PCR products were also generated from HeLa cells applied to FTA sample collection cards. HeLa cells in PBS were applied to FTA sample collection cards. The cards were allowed to dry for 3 hours prior to the removal of a small section of the card which contained lysed HeLa cellular debris. This excision was accomplished using a Harris 1.2 mm diameter extraction punch. The 1.2 mm punch was subject to a 15 minute SDS (2% w/v) incubation at 37° C., followed by a 5 minute room-temperature incubation with a 1:2 molar ratio of cyclodextrin, followed by an incubation of 65° C. for 10 min. The mixture plus punch was allowed to cool and then subjected to direct RT-PCR as previously described using AffinityScript RT in combination with Taq DNA polymerase. The reaction was supplemented with i); β-actin, exon 1 forward 5'-CCTCGCCTTTGCC-GATCC-3' and exon 4 reverse 5'-GGATCTTCAT-GAGGTAGTCAGTC-3'; RT-PCR product size 626 bp ii) the direct RT-PCR chemical additives described in Tables 3 & 4 and iii) random hexamers.

The thermocycle used was as follows; to initiate the RT reaction the punch and reagents were thoroughly mixed and incubated at 42° C. for 60 minutes followed by the addition of Taq DNA polymerase, ×10 PCR buffer etc. The PCR conditions consisted of; 95° C. for 3 minutes and the following thermocycle; 40 cycles at 95° C. for 30 seconds, 55° C. for 1 minute and 72° C. for 1 minute with an extension of 72° C. for 5 minutes.

Figure 13:
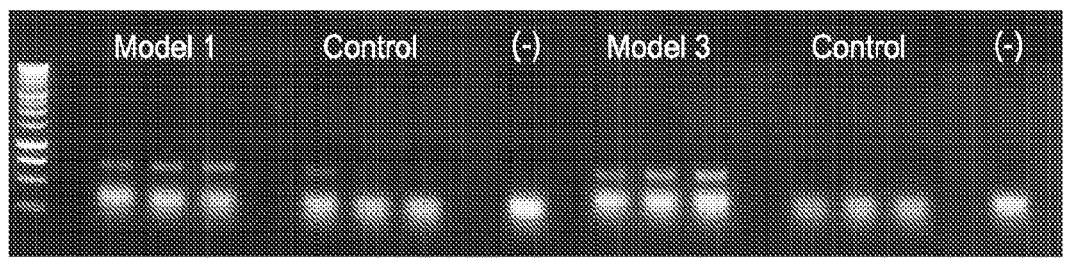
FIG. 13 shows a representative composite agarose gel showing the yield of RT-PCR products generated using HeLa cell applied to FTA Sample collection cards in combination with the addition of the specific chemicals to "liquid" RT-PCR reactions. These chemical combinations were identified by the PredictionProfiler using the SAS JMP software and during the DOE evaluating the use of RT-PCR RTG beads. Model 1—BSA 0.6% (w/v), DMSO 5% (v/v) and glycerol 10% (v/v) and Model 3—BSA 0.6% (w/v), DMSO 5% (v/v) and glycerol 10% (v/v); are shown as an illustration, Control—BSA (0.6% w/v), M=DNA molecular weight markers and (−) negative RT-PCR control.

RT-PCR amplicons for β-actin of the correct 626 bp size were generated in all the RT-PCR reactions. The relative yield of each RT-PCR product was determined by the intensity of bands visualised on agarose gels. The yield of RT-PCR products associated with the reactions supplemented with the chemical additives were all greater than that derived from the control reaction supplemented with BSA (0.6% w/v) only. A representative agarose gel (FIG. 13) showing the results from Model 1 and Model 3 compared to the control reaction is shown as way of illustration. Increased β-actin RT-PCR product yield was also observed from all RT-PCR RTG bead reactions supplemented with all the chemical additives described in Tables 3 & 4 (data not shown).

The invention claimed is:

1. A method of amplifying an RNA molecule in a biological sample by a reverse transcription PCR (RT-PCR) reaction, wherein the RT-PCR reaction is carried out in a solution comprising:
   a. a polar aprotic solvent;
   b. a serum albumin; and
   c. a polyol;
   the method comprising:
   i) contacting a solid support having a lysis agent embedded thereon with the biological sample containing the RNA molecule, wherein the RNA molecule becomes immobilized on the solid support;
   ii) transferring the solid support or a portion thereof with the lysis agent to a reaction vessel; and
   iii) performing the RT-PCR reaction in the reaction vessel in the solution in the presence of the solid support with the lysis agent,
   wherein the biological sample has not undergone an RNA purification step prior to the RT-PCR reaction.

2. The method according to claim 1, wherein the polar aprotic solvent is DMSO (dimethyl sulfoxide).

3. The method according to claim 1, wherein the serum albumin is bovine serum albumin (BSA).

4. The method according to claim 1, wherein the polyol is glycerol.

5. The method according to claim 1, wherein the solution further comprises a reducing agent.

6. The method according to claim 5, wherein the reducing agent is dithiothreitol (DTT) or Tris(2-carboxyethyl) phosphine hydrochloride (TCEP).

7. The method according to claim 1, wherein the solution further comprises a non-ionic surfactant.

8. The method according to claim 1, wherein the solution further comprises a non-ionic surfactant and a betaine.

9. The method according to claim 7, wherein the non-ionic surfactant is Triton X-100, Brij 56 or Brij 58.

10. The method according to claim 8, wherein the betaine is N,N,N-trimethylglycine.

11. The method according to claim 1, wherein the solution comprises:
   a. DMSO at a concentration in the range 0.05 to 10% (v/v), glycerol at a concentration in the range 0.05 to 15% (v/v), and BSA at a concentration in the range 0.05 to 1.2% (w/v); or
   b. DMSO at a concentration in the range 0.05 to 10% (v/v), glycerol at a concentration in the range 0.05 to 15% (v/v), BSA at a concentration in the range 0.05 to 1.2% (w/v), and DTT or TCEP at a concentration in the range 0.5 to 20 mM; or
   c. DMSO at a concentration in the range 0.05 to 10% (v/v), glycerol at a concentration in the range 0.05 to 15% (v/v), BSA at a concentration in the range 0.05 to 1.2% (w/v), Triton X-100 at concentration in the range 0.05 to 1% (v/v); or
   d. DMSO at a concentration in the range 0.05 to 10% (v/v), glycerol at a concentration in the range 0.05 to 15% (v/v), BSA at a concentration in the range 0.05 to 1.2% (w/v), Triton X-100 at concentration in the range 0.05 to 1% (v/v), and N,N,N-trimethylglycine at a concentration in the range 0.05 to 2M.

12. The method according to claim 1, wherein the solution further comprises:
   a. a reverse transcriptase;
   b. a DNA polymerase;
   c. a deoxyribonucleotide triphosphate (dNTP); and
   d. at least one primer.

13. The method according to claim 1, wherein the biological sample has not undergone treatment with a DNase prior to the RT-PCR reaction.

14. A method according to claim 1, further comprising subjecting the biological sample to a lysis step and a detergent neutralization step prior to contacting the biological sample with the solution.

15. The method according to claim 14, wherein the lysis step is performed by contacting the biological sample with a detergent, and the detergent neutralization step is performed by contacting the sample with a cyclodextrin.

16. The method of according to claim 1, wherein the biological sample comprises a cellular sample selected from the group consisting of blood, serum, semen, cerebral spinal fluid, synovial fluid, lymphatic fluid, saliva, buccal, cervical cell, vaginal cell, urine, faeces, hair, skin, muscle, and cells grown in culture.

17. The method according to claim 1, wherein the biological sample is derived from a virus, a eukaryotic organism or a prokaryotic organism.

18. The method according to claim 16, wherein the biological sample is a blood sample, optionally where the blood has been treated with an anti-coagulant.

19. The method according to claim 1, wherein the solid support:
   (a) is fibrous, optionally comprising a cellulose fibre material or a glass fibre or glass microfiber material; or
   (b) comprises a porous polymer or porous membrane material such as polyester, polyether sulfone (PES), polyamide (Nylon), polypropylene, polytetrafluoroethylene (PTFE), polycarbonate, cellulose nitrate, cellulose acetate or alignate; or
   (c) comprises aluminium oxide.

20. A method of amplifying an RNA molecule in a biological sample by reverse transcription PCR (RT-PCR) reaction, wherein the RT-PCR reaction is carried out in a solution comprising:
   a. a polar aprotic solvent;
   b. a serum albumin; and
   c. a polyol;
   the method comprising:
   i) contacting a solid support having (i) a weak base; (ii) a chelating agent; (iii) an anionic surfactant and (iv) a chaotropic agent such as guanidium thiocyanate impregnated thereon with the biological sample containing the RNA, wherein the RNA becomes immobilized on the solid support;
   ii) transferring the solid support or a portion thereof with the (i) a weak base; (ii) a chelating agent; (iii) an anionic surfactant and (iv) a chaotropic agent to a reaction vessel; and
   iii) performing the RT-PCR reaction in the reaction vessel in the solution in the presence of the solid support with the (i) a weak base; (ii) a chelating agent; (iii) an anionic surfactant and (iv) a chaotropic agent wherein the biological sample has not undergone an RNA purification step prior to the RT-PCR reaction.

21. The method according to claim 20, wherein the polar aprotic solvent is DMSO (dimethyl sulfoxide).

22. The method according to claim 20, wherein the serum albumin is bovine serum albumin (BSA).

23. The method according to claim 20, wherein the polyol is glycerol.

24. The method according to claim 20, wherein the solution further comprises a reducing agent.

25. The method according to claim 24, wherein the reducing agent is dithiothreitol (DTT) or Tris(2-carboxyethyl) phosphine hydrochloride (TCEP).

26. The method according to claim 20, wherein the solution further comprises a non-ionic surfactant.

27. The method according to claim 20, wherein the solution further comprises a non-ionic surfactant and a betaine.

28. The method according to claim 26, wherein the non-ionic surfactant is Triton X-100, Brij 56 or Brij 58.

29. The method according to claim 27, wherein the betaine is N,N,N-trimethylglycine.

30. The method according to claim 20, wherein the solution comprises:
   a. DMSO at a concentration in the range 0.05 to 10% (v/v), glycerol at a concentration in the range 0.05 to 15% (v/v), and BSA at a concentration in the range 0.05 to 1.2% (w/v); or
   b. DMSO at a concentration in the range 0.05 to 10% (v/v), glycerol at a concentration in the range 0.05 to 15% (v/v), BSA at a concentration in the range 0.05 to 1.2% (w/v), and DTT or TCEP at a concentration in the range 0.5 to 20 mM; or
   c. DMSO at a concentration in the range 0.05 to 10% (v/v), glycerol at a concentration in the range 0.05 to 15% (v/v), BSA at a concentration in the range 0.05 to 1.2% (w/v), Triton X-100 at concentration in the range 0.05 to 1% (v/v); or
   d. DMSO at a concentration in the range 0.05 to 10% (v/v), glycerol at a concentration in the range 0.05 to 15% (v/v), BSA at a concentration in the range 0.05 to 1.2% (w/v), Triton X-100 at concentration in the range 0.05 to 1% (v/v), and N,N,N-trimethylglycine at a concentration in the range 0.05 to 2M.

31. The method according to claim 20, wherein the solution further comprises:
   a. a reverse transcriptase;
   b. a DNA polymerase;
   c. a deoxyribonucleotide triphosphate (dNTP); and
   d. at least one primer.

32. The method according to claim 20, wherein the biological sample has not undergone treatment with a DNase prior to the RT-PCR reaction.

33. A method according to claim 20, further comprising subjecting the biological sample to a lysis step and a detergent neutralization step prior to contacting the biological sample with the solution.

34. The method according to claim 33, wherein the lysis step is performed by contacting the biological sample with a detergent, and the detergent neutralization step is performed by contacting the sample with a cyclodextrin.

35. The method of according to claim 20, wherein the biological sample comprises a cellular sample selected from the group consisting of blood, serum, semen, cerebral spinal fluid, synovial fluid, lymphatic fluid, saliva, buccal, cervical cell, vaginal cell, urine, faeces, hair, skin, muscle, and cells grown in culture.

36. The method according to claim 20, wherein the biological sample is derived from a virus, a eukaryotic organism or a prokaryotic organism.

37. The method according to claim 35, wherein the biological sample is a blood sample, optionally where the blood has been treated with an anti-coagulant.

38. The method according to claim 20, wherein the solid support:
   (a) is a cellulose fibre material or a glass fibre or glass microfiber material; or
   (b) comprises a porous polymer or porous membrane material such as polyester, polyether sulfone (PES), polyamide (Nylon), polypropylene, polytetrafluoroethylene (PTFE), polycarbonate, cellulose nitrate, cellulose acetate or alignate; or
   (c) comprises aluminium oxide.

* * * * *